(12) United States Patent
Bright et al.

(10) Patent No.: US 7,750,294 B2
(45) Date of Patent: Jul. 6, 2010

(54) PHOTONIC SENSORS, XEROGEL-BASED SENSORS AND NANOSENSORS

(75) Inventors: Frank V. Bright, Williamsville, NY (US); William G. Holthoff, Tonawanda, NY (US); Elizabeth C. Tehan, Buffalo, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 11/076,729

(22) Filed: Mar. 10, 2005

(65) Prior Publication Data

US 2010/0001185 A1    Jan. 7, 2010

Related U.S. Application Data

(60) Provisional application No. 60/551,818, filed on Mar. 10, 2004.

(51) Int. Cl.
*G01N 21/00* (2006.01)
(52) U.S. Cl. ..................... 250/308
(58) Field of Classification Search ............. 250/308
See application file for complete search history.

(56) References Cited

U.S. PATENT DOCUMENTS 5,047,350 A * 9/1991 Switalski et al. ............ 436/136
5,864,146 A * 1/1999 Karellas ..................... 250/581
2005/0079131 A1* 4/2005 Lanza et al. ................ 424/1.11

OTHER PUBLICATIONS

Hobbs et al. Scintillator light source for chemical sensing in the near-ultraviolet, Analytical Chemistry, vol. 69, No. 16 (Aug. 15, 1997), pp. 3375-3379.*
Cho et al. Pin-printed chemical sensor arrays for simultaneous multianalyte quantification, Analytical Chemistry, vol. 74, No. 6 (Mar. 15, 2002), pp. 1462-1466.*
Hirschfeld et al. Laser-fiber-optic "optrode" for real time in vivo blood carbon dioxide level monitoring, Journal Of Lightwave Technology, vol. LT-5, No. 1 (Jul. 1987), pp. 1027-1033.*
Burden, D.L., and Hieftje, G.M., "Comparison of digital correlation techniques in time-resolved fluorometry using a radionuclide-scintillation excitation source," Rev. Sci. Instrum., Jan. 1999, pp. 50-57, vol. 70, No. 1.
Tang et al., "Sol-Gel Derived Sensor Materials That Yield Linear Calibration Plots, High Sensitivity, and Long-Term Stability", May 15, 2003, 2407-2413, 75-10, Anal. Chem.

* cited by examiner

*Primary Examiner*—David P Porta
*Assistant Examiner*—Shun Lee
(74) *Attorney, Agent, or Firm*—Hodgson Russ LLP

(57) ABSTRACT

A photonic sensor system is provided. The system generally includes a beta emission source, optionally, a scintillation layer, and a luminophore-containing sensory layer. The system can be embodied in a particle. Also provided are photonic sensor strategies which are highly accurate and photonic sensors which are highly stable.

11 Claims, 35 Drawing Sheets (3 of 35 Drawing Sheet(s) Filed in Color)

Simplified schematic of the beta emitter-based sensor array system.

Figure 1. Simplified schematic of the beta emitter-based sensor array system.

Figure 2. Examples of possible beta emitter-scintillator-sensor element geometries.

Figure 3. False color image of a [Ru(dpp)$_3$]$^{2+}$-doped xerogel-based sensor array when excited by the combination of a 2 mCi $^{90}$Sr beta emitter and an EJ-200 scintillator. The diameter of a typical sensor element is ~200 μm.

Figure 4. Typical calibration curve for an $O_2$ responsive sensor element excited by the combination of a 2 mCi $^{90}$Sr beta emitter and an EJ-200 scintillator.

Figure 12. Schematic of the pin system along with eight possible pin types/geometries.

Figure 13. Potential geometries at the distal end of a channel-based pin.

5 kHz 10 kHz 20 kHz 50 kHz 100 kHz 250 kHz 20 kHz 150 kHz

PHOTONIC SENSORS, XEROGEL-BASED SENSORS AND NANOSENSORS

This application claims priority to Provisional Application No. 60/551,818, filed on Mar. 10, 2004.

This invention was made with Government support under grant numbers CHE-0315128 from the National Science Foundation (NSF) and N00014-02-1-0836 from the Office of Naval Research (ONR). The Government has certain rights in the invention.

FIELD OF THE INVENTION

The present invention relates generally to area of detection of analytes.

BACKGROUND

The desire to simultaneously measure "everything" in any sample has driven the development of artificial "noses" and "tongues". These devices have been based on a wide variety of sensor array strategies. Examples of sensor arrays include those based on cantilevers, conducting polymers, electrochemistry, photonics, the piezoelectric effect, or surface acoustic waves. In a photon-based sensor, one requires a photon source, appropriate sensing chemistry (i.e., a recognition element), a means to immobilize the desired sensing chemistry so it may be reused, and a photon detector. All reported photon-based sensor arrays depend on at least one photon source (e.g., lamps, lasers, light emitting diodes) and all currently used photon sources in photon-based sensor arrays require electrical power. This need for electrical power limits any photonically-based sensor device.

Although a number of strategies exist for developing photonically-based sensor arrays (vide supra), there is clearly a need for new strategies that use little or no electrical power. Specifically, there is a need for devices wherein the photon/light source operates without any external electrical power. Hieftje and coworkers (Rev. Sci. Instrum. 1999, 70:50-57) introduced the idea of using a beta emitter, $^{90}$Sr, and a liquid or plastic scintillator in concert with time-correlated single photon counting as a pulsed photon source for the determination of excited-state fluorescence lifetimes.

A system has been developed to address the limitations of existing sensor array photon sources. Our source system can potentially work with any photonically-based chemical sensor modality. It consists of a sealed $^{90}$Sr beta emitter (with or without a scintillator), a chemical responsive sensor array, and an array-based photodetector. It can serve as part of a complete photonically-based sensor array system that has two major features. First, the photon source does not require any electrical power and the source can be operated continuously, in an unattended manner, for several years. Thus, electrical power is only needed to power the photodetector in this system. Second, the so formed photonic sensor array is capable of the detection and/or quantification of more than one analyte in a sample at the same time.

SUMMARY OF THE INVENTION

The present invention provides a photonic sensor system for the detection of, and in one embodiment, the two dimensional resolution of, a chemical analyte. It functions by measuring the radiation from sensors which are in contact with a sample. The sensors are stimulated to radiate either by a beta emission source or a by radiation from a scintillation layer which is interposed between a beta emission source and the sensor. During exposure of the sensors to the desired analyte, the radiation from the sensor changes in intensity, wavelength or both. By comparing the radiation during analyte exposure to the radiation from the sensor unexposed to the analyte, the concentration of analyte in a sample can be determined. If a sensory array is used, two dimensional resolution of concentration can be determined. Distributions of sensors can be used to give an "image" of analyte in a sample. If a sensory array with sensors which are sensitive to multiple different analytes are used, multiple analytes can be simultaneously detected in a sample. Also provided are sensory arrays which have increased reliability and lower error than existing sensors due to the use of an array with diversified sensors for a single analyte.

In general, unlike existing methods, the source of photons which impinge on the sensory array (i.e., the beta emission source, either with or with out a scintillation layer) does not require an external power source, and can remain stable over long periods of time without attention.

The present invention further provides a method for preparing sensory arrays which allow greater spatial resolution than previously attainable. The method comprises the creation of pin printing arrays in which the pins have been created from specific materials by pulling, cutting or etching, optionally followed by the treatment of the pin tips with materials which allow the easy dispensing of ultra-small array sensors.

As an embodiment of the sensor systems described above, also provided are nanosensors which have integrated beta emission sources and a sensory layer analogous to a sensor. These nanosensors are introduced directly into the sample, and the radiation from the sensory layers of the particles is collected and analyzed to determine an analyte profile.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Provided by the present invention are photonic sensor arrays based on a non-electrical light source. A view of the invention is given in FIG. 1. The source system consists of a sealed $^{90}Sr$ beta emitter housed within a ceramic disc which is in turn incorporated within a stainless steel body along with an optional scintillator and an array of photonically active sensor elements. The sequestration of the $^{90}Sr$ within the ceramic matrix in conjunction with the stainless steel capsule precludes any radioactive material leaching. Other radioactive sources could be used. Such a source is commercially available from AEA Technology, QSA Incorporated (Burlington, Mass.). The beta radiation from the sealed $^{90}Sr$ emitter is directed toward the chemical sensor array. Other beta-emitters can also be used in the photonic sensor system of the present invention, such as $^{3}H$, $^{14}C$, $^{22}Na$, $^{32}Si$, $^{32}P$, $^{35}S$, $^{36}Cl$, $^{41}Ca$, $^{57}Co$, $^{60}Co$, $^{63}Ni$, $^{89}Sr$, $^{90}Sr$, $^{90}Y$, $^{99}Tc$, $^{129}I$, $^{137}Cs$, $^{147}Pm$, $^{151}Sm$, $^{204}Tl$, $^{210}Pb$, $^{210}Bi$, $^{237}U$, $^{238}Np$, or $^{241}Pu$.

While not required, in some embodiments, between the source and the sensor array is a scintillation medium, such as, for example, a liquid scintillator solution or a plastic scintillator material. A wide variety of scintillation materials can be used, such as, for example, EJ-200, EJ-204, EJ-208, EJ-212, EJ-232, EJ-301, EJ-321, EJ-331, and EJ335 from Eljen or similar products from sources like Zinsser Analytic or Amcrys-H. In general, the choice of scintillation material between the beta emitter and the array of sensor elements depends on the chemical and photonic nature of the sensing chemistry and the associated luminophores in that radiation emitted by the scintillation material should be comprised of a wavelength that the luminophores present in the sensor can absorb.

Figure 1:
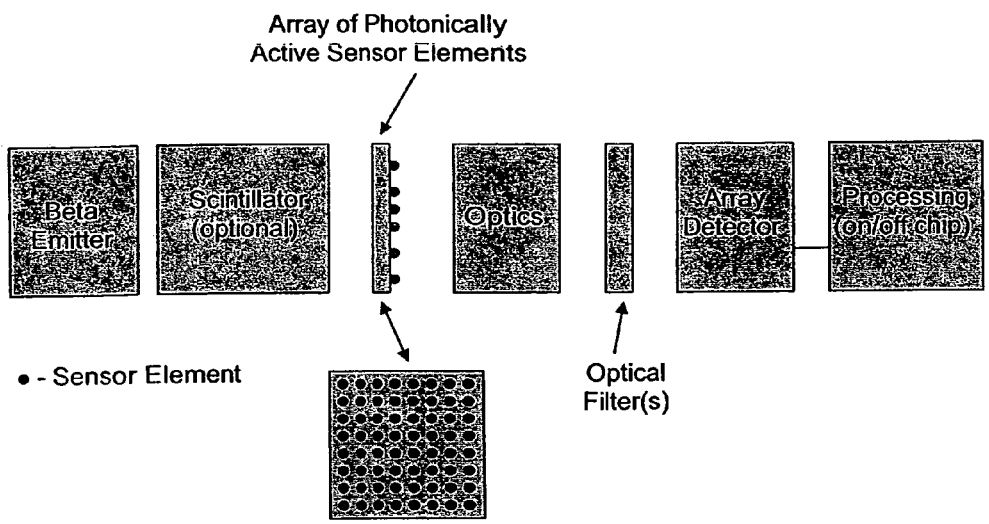
FIG. 1 is a simplified schematic of the beta emitter emitter-based sensor array system.

In one embodiment, the beta particles are emitted from the sealed source and they impinge upon scintillator molecules which produce photons, these photons impinge upon the sensors, exciting luminophores contained within the sensors. In another embodiment, the beta particles impinge directly upon the luninophores sequestered within the sensor elements (FIG. 1). The presence of a scintillating layer gives increased flexibility to the system because it is generally possible to choose a scintillator which produces a wavelength of light which corresponds to an absorption wavelength of the chosen luminophore or chromophore. Regardless of which embodiment is used, the resulting emission (or absorbance) from the sensor elements is detected by one of many possible array-based photon detectors (e.g, charge transfer device, complementary metal oxide semi conductor) known to those familiar with the discipline of photon detection.

Luminophores or chromophores which can be used in the process photonic sensor system of the present invention absorb or emit in the ultraviolet, visible or infrared. Non-limiting examples of reporters which can be used include luminescent organic or inorganic species like fluorescein, BODIPY, rhodamine; organometallic complexes like tris (4,7-diphenyl-1,10-phenanthroline)ruthenium(II) ([Ru (dpp)$_3$]$^{2+}$; and luminescent nanoparticles (i.e., quantum dots). Non-luminescent dye molecules that are responsive to their physicochemical environments can also be used (e.g., 4-nitroaniline, and 2,6-diphenyl-4-(2,4,6-triphenyl-1-pyridinio)phenolate (Reichardt's dye 30), 2,6-dichloro-4-(2,4,6-triphenyl-1-pyridinio)phenolate (Reichardt's dye 33), and N,N-diethyl-4-nitroaniline).

In general, the sensors in the present invention can be of any type which comprise luminophores or chromophores which give changes in their absorbance and/or emission spectra, polarization, and/or excited-state lifetime upon exposure to the analyte for which a sensor is desired. Examples of types of sensors which can be used in the present invention are molecularly imprinted polymers, gels and xerogels; monolayer-based sensor elements, protein-based biosensors and others known to those expert in the field of chemical sensing. Analytes which can be detected are diverse, including molecules as small as oxygen to molecules as large as proteins and peptides.

Figure 2:
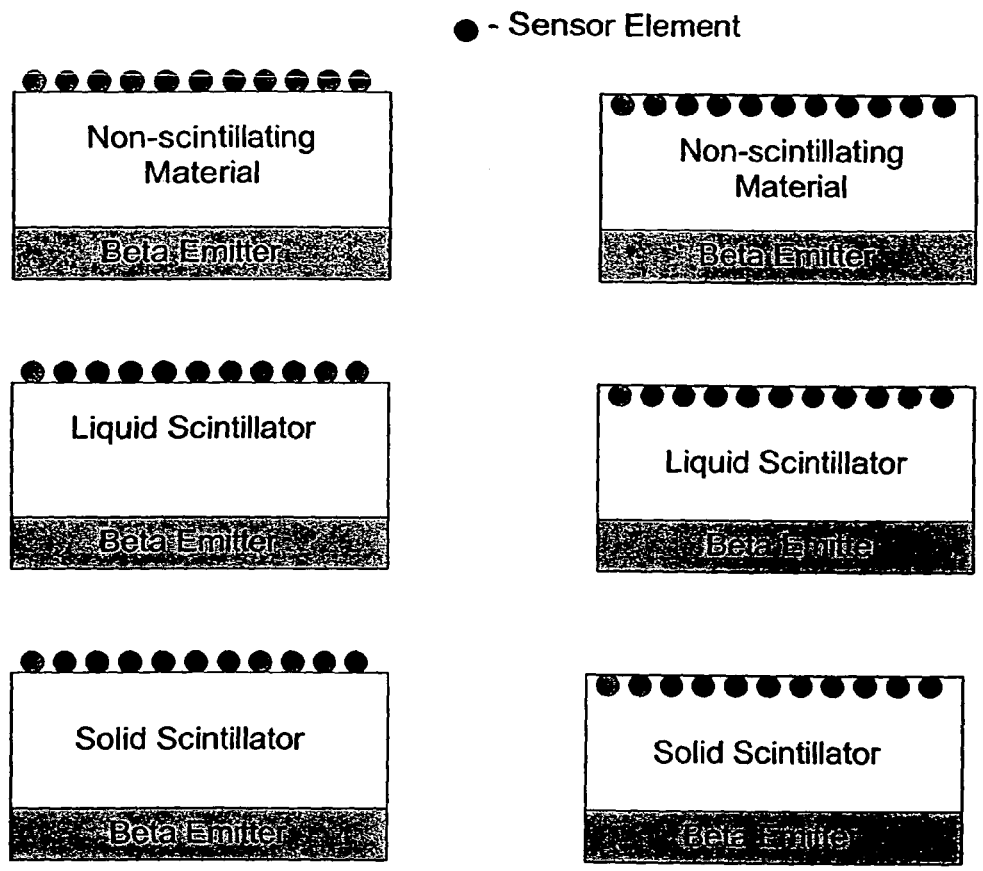
FIG. 2 shows examples of possible beta emitter-scintillator-sensor element geometries.

Solid scintillation materials have the advantage that a sensor or sensor array can be formed on the face of the scintillator, or within the scintillator as shown in FIG. 2.

The absorbance from the sensor elements within the array are passed through collection optics, an optical filter, and detected by a suitable array detector (e.g., a charge transfer device or a complementary metal oxide semiconductor). The signals from the photodetector can also be processed by a variety of methods, including, for example, on-chip electronics or within a computer.

The present invention is not limited in scope to the measurement of sensor emission. It should be noted that other sensor properties, such as changes in absorption of radiation (instead of changes in emission) due to the exposure of the sensor to an analyte can be measured and processed to give the benefits of the invention described herein.

Figure 3:
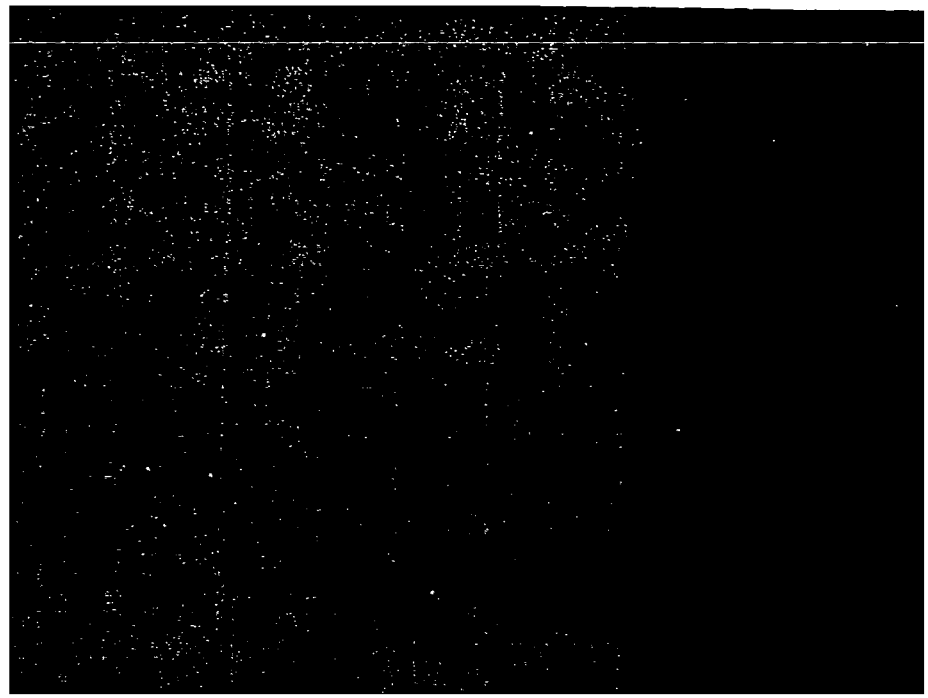
FIG. 3 is a false color image of a $[Ru(dpp)_3]^{2+}$-doped xerogel-based sensor array when excited by the combination of a 2 mCi$^{90}$Sr beta emitter and an EJ-200 scintillator. The diameter of a typical sensor element is ~200 μm.

The use of an array can also give a spatially resolved image of the concentration of a particular analyte. FIG. 3 presents a false color image from a portion of an $O_2$ responsive sensor array that was prepared from a binary nanoporous xerogel glass composed of 1:1 mole ratio of tetramethyorthosilane (TMOS) and octyl-trimethoxysilane (C8-TrMOS) doped with an $O_2$ responsive luminophore (tris(4,7-diphenyl-1,10-phenanthroline)ruthenium(II) dication, $[Ru(dpp)_3]^{2+}$). In the presence of $O_2$ the $[Ru(dpp)_3]^{2+}$ emission is quenched in step with the $O_2$ concentration. (A calibration curve (Stern-Volmer plot) for these sensor elements when they are excited by the combination of a single 2 mCi $^{90}Sr$ beta emitter and an EJ-200 scintillator is presented in FIG. 4.)

Also provided by the present invention is method of imaging which differs from current methods.

There are numerous problems that require one to identify and determine the concentration of a particular molecule (i.e., the target analyte) within a sample/specimen in a spatially defined manner. Examples include the detection of a specific target analyte within polymer-based composites, living cells, or tissues. One common strategy (shown in FIG. 5) is to use luminescence in concert with intrinsic reporters or extrinsic sensors. Examples of intrinsic reporters include luminescent species like the aromatic residues attached to certain oligomers/polymers, proteins (aromatic amino acids or other chromophores therein), reduced nicotine adenine dinucleotide (NADH), flavins, and bilirubin. These species are intrinsic to a particular system/specimen, they are luminescent, and their emission can be used to map their location within the system/specimen. Autoemission can also have intrinsic diagnostic value. For example, sample/specimen autofluorescence spectra have been used to screen for bladder, colorectal, lung and skin cancers, to assess dental hard tissue, and screen foods. An extrinsic sensor is added to the system by one of many strategies (e.g., physical mixing, gene gun injection into a cell) and the tiny sensors distribute themselves within the sample/specimen and they report on their target analyte. [Note: This distribution process can be made pseudo selective by using selective biomolecules (e.g., antibodies) to deliver the sensors to a specific site within the sample/specimen (e.g., interface, mitochondria).]

Figure 5:
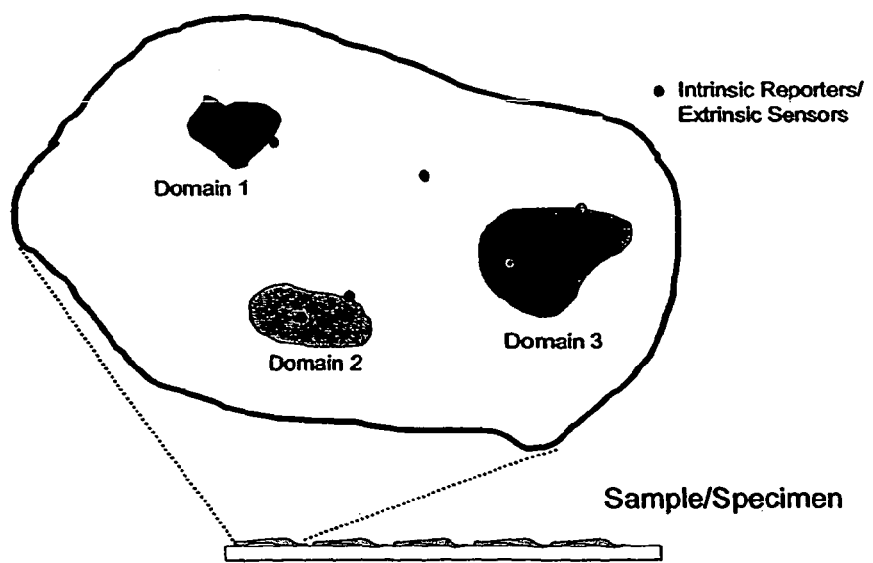
FIG. 5 represents imaging strategy which uses with intrinsic reporters or extrinsic sensors.

If the sensor shown in Domain 1 of FIG. 5 were designed to detect target analyte A, the concentration of A at that specific site on the edge of Domain 1 could be determined. Similarly, the sensor shown in Domain 3 of FIG. 5 could report on analyte B within Domain 3. The idea of "injecting" sensors into a sample/specimen is at the heart of the so called nanopebble-based photonic sensors developed by the Kopelman group [cf., Park, E. J. et al. Anal. Chem. 2003, 75, 3784-3791 and references cited therein]. A related example involves the use of selective or semi-selective synthetic chromophores/luminophores that respond to a specific non-fluorescent target analyte (e.g., Calcium Green for $Ca^{2+}$, fluorescein for pH, IndoZn for $Zn^{2+}$).

Figure 6:
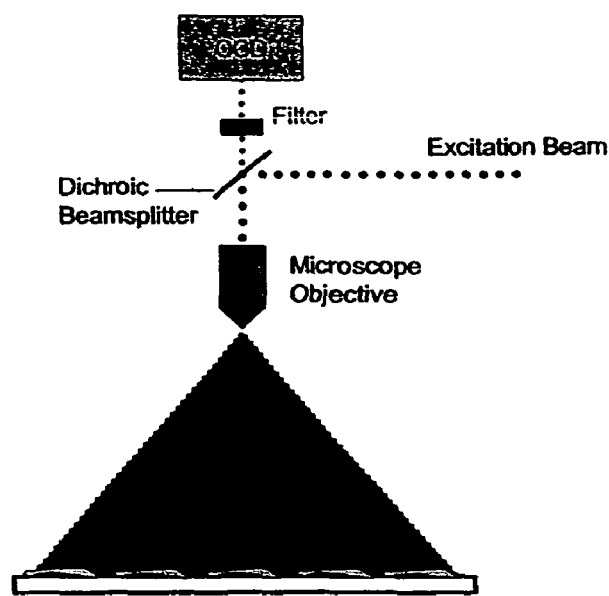
FIG. 6 shows an illustration of a one-photon excitation strategy.
Figure 7:
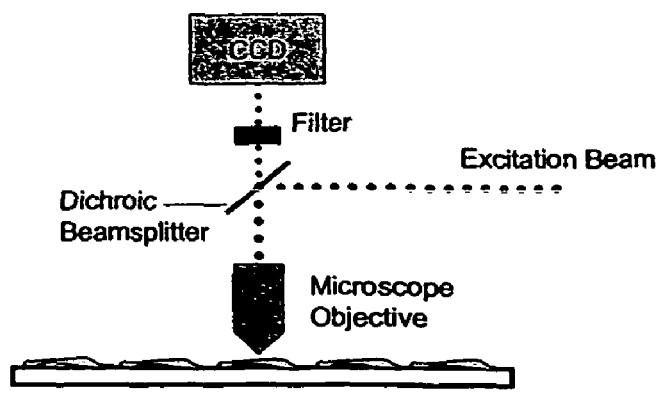
FIG. 7 shows an illustration of a multi-photon excitation strategy.

Typical optical configurations for exciting the luminescent reporters and/or sensors are shown in FIGS. 6 and 7. FIG. 6 represents a one-photon excitation situation and FIG. 7 means to illustrate a multi-photon excitation strategy. Regardless of the case, the current state-of-affairs requires that an excitation beam from an external light source must be brought into the sample so as to excite the intrinsic reporters or extrinsic sensors within the sample/specimen.

There have yet to be any strategies described that avoid the use of an external light source (laser, lamp, light emitting diode, etc.) to excite the luminescent species within the sample/specimen. Furthermore, although a number of strategies exist for developing photonically-based sensors, there is no strategy for producing the emission and imaging such from the sample/specimen without the use of a photon source that is external to the sample/specimen.

Several methods involve the idea of using a beta emitter and a liquid, plastic, or inorganic solid scintillator to fabricate photonically-based instruments wherein the light source requires no electrical power. For example, it has been shown how to use a beta emitter, $^{90}Sr$, and a liquid or plastic scintillator in concert with time-correlated single photon counting as a pulsed photon source for the determination of excited-state fluorescence lifetimes. It is also known how to produce single element quenchometrically-based macrosensors for a single analyte. Microsensor arrays for the simultaneous detection of multiple target analytes in a sample wherein the light source was based on a no electrical power $^{90}Sr$ beta emitter are also known.

Figure 8:
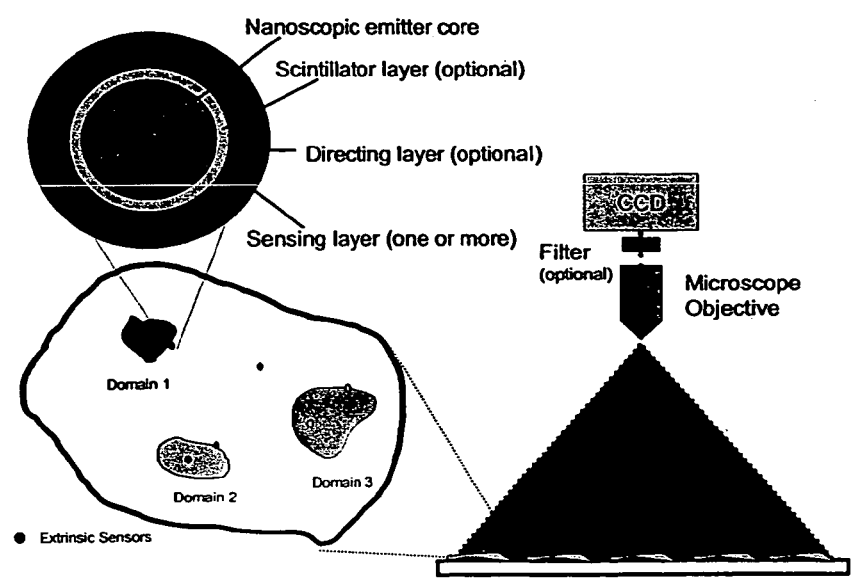
FIG. 8 shows an illustration of nanosensor particle structure (top left) and the sequestering, in specific sample domains, of particles which comprise a directing layer.

In one embodiment, the present invention provides a system which, when introduced into a sample, produces emission in a pattern corresponding to the spatial distribution of an analyte, without the presence of a power source or external photon source. Provided by the present invention are chemically responsive nanosensors with integrated light sources. This embodiment of the invention current invention is hereafter referred to as a chemically responsive nanosensor with an integrated light source (CRNILS) (FIG. 8 top left). It is a nanosensor particle which can be introduced into a sample or specimen. A CRNILS is structured around one or more beta emitter cores. Beta emitter cores which can be used in the photonic sensor described above can also be used in the CRNILS (e.g., $^{3}H$, $^{14}C$, $^{22}Na$, $^{32}Si$, $^{32}P$, $^{35}S$, $^{36}Cl$, $^{41}Ca$, $^{57}Co$, $^{60}Co$, $^{63}Ni$, $^{89}Sr$, $^{90}Sr$, $^{90}Y$, $^{99}Tc$, $^{129}I$, $^{137}Cs$, $^{147}Pm$, $^{151}Sm$, $^{204}Tl$, $^{210}Pb$, $^{210}Bi$, $^{237}U$, $^{238}Np$, or $^{241}Pu$. These emitters are preferably sealed within a material such as ceramic, such that the sample is not needlessly exposed to beta emission or contaminated with core material. Macroscopic emitters are commercially available from AEA Technology, QSA Incorporated (Burlington, Mass.).

The layered structure of the nanosensor facilitates an operation which similar to the operation of the photonic sensor embodiment. The nanosensor comprises a sensor layer which encases the beta emitter core, as well as an optional layer of scintillation material which is between the core and the one or more sensor layers. Either beta particles from the core or beta-stimulated radiation impinge upon the luminophores within the sensing layers (FIGS. 8 and 9) and these species emit and/or absorb in a manner which is dependent on whether or not they are exposed to a desired analyte. The choices of scintillation material and sensor layer materials are generally dictated by the same constraints as outlined above for the photonic sensor. The CRNILS invention can be used with luminescence-based sensor strategy that can be coated as a thin film sensing layer.

The nanosensor embodiment may optionally comprise a "directing layer," which can cause the nanosensor to preferentially locate near or within certain regions of a sample or specimen. Examples of directing layers include antibodies, DNA, RNA, enzymes, peptides and related species or other natural and/or synthetic species that have selective interactions (ionic, H-bonding, π-π, Van der Waals, etc.) with a particular site/domain within the sample/specimen.

A cross sectional view of an example of the invention is presented in FIG. 8. A CRNILS (top left) consists of a nanoscopic sealed beta emitter (e.g., $^{90}$Sr) that is surrounded by a thin layer of an optional scintillator layer, one or more sensing layers that contain one or more photonically active sensor molecules, and an optional directing layer.

Figure 9:
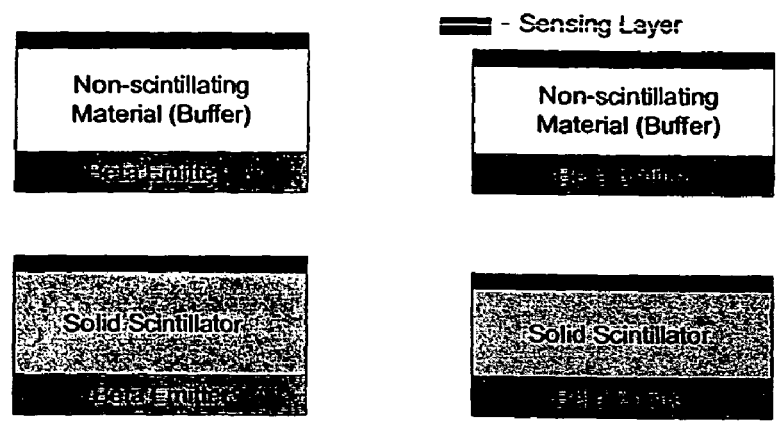
FIG. 9 is a depiction of exemplary beta emitter-sensing layer configurations.

The sensing layer can be formed on the face of the scintillator, within the scintillator, on the face of the non-scintillating material, or within the non-scintillating material as shown in FIG. 9. Strategies for producing such luminescence-based sensing layers are well-known. Examples are the subject matter of U.S. patent application Ser. Nos. 11/006,857 and 11/031,318, incorporated herein by reference.

In operation one or more CRNILS for specific target analytes are mixed or injected into the sample/specimen. They distribute within the sample/specimen based on the directing layer chemistry (specific or non-specific/random). The resulting emission (or absorbance) from the CRNILS is/are detected by an external array-based photon detector. The array detector allows imaging of the multitude of CRNILS that could be located with a given sample/specimen.

The chemically-responsive emission from the nanosensors can be collected by a microscope objective and detected by a suitable array detector (charge transfer device, video camera, or a complementary metal oxide semiconductor). The signals from the photodetector can also be processed by on-chip electronics or within a computer, or other methods known in the art.

An advantage of this invention over existing technologies is that an external source of photons is not necessary. Excitation of the sensing layer only comes from within the nanosensor. Excitation of different luminophores that may high grossly different absorbance/excitation spectra within the sensing layers can be carried out in real time. Long-term monitoring can be achieved depending on the source of the beta emissions (e.g., the half lives of $^{90}$Sr are 28.5 yrs, $^{32}$P is 14.3 days, and $^{238}$Np is 2.1 days). The noise magnitude in these nanosensors should be much less in comparison to any external light source-based methods. The emitters are intrinsically pulsed at a high rate. This allows lifetime-based sensing to be exploited. It is possible to exploit steady-state and time-resolved luminescence anisotropies if the excitation from the emitter and/or scintillator is polarized enough. There is no risk of radioactive contamination from the beta emitter since it is bound in a ceramic matrix and encapsulated. The size of the nanosensors used in the above embodiment of the present invention is limited only by application. For example, if they are to be introduced by injection, they should be small enough to pas into the sample via a syringe or other injection device.

The present invention also provides tailored pins for high density microarray production. The word "array," as used here, means a two-dimensional arrangement of elements. In the current context, an array is formed on a planar or curved support. The array provides a way of detecting, matching, quantifying, and/or screening known and unknown molecules based on, among other possible schema, the intermolecular interactions between the array elements (spots) and the molecules in the sample.

The sensor arrays which can be formed by the method of the present invention make use of a wide variety of molecular recognition systems (e.g., ion-cryptan, ion-ligand, host-guest inclusion, DNA base pairing, protein-ligand, protein-protein, antibody-hapten or antibody-antigen binding) or molecularly imprinted materials. Experiments could involve an enzymatic reaction scheme wherein a colored product is produced or wherein a change in the absorbance and/or emission of chromophore is modulated by the presence of an analyte as described above. Arrays of this type can also be used to screen for lead materials or molecules in applications ranging from biomaterials to sensing to drug discovery or biomarker identification.

The size of the array elements (the "feature size") dictates the element density on the array and thus the number of simultaneous assays, assessments, and/or measurements one can carry out.

One of the main goals in microarray design is to develop new tools to decrease the feature size and increase the array element density (i.e., the number of sensor elements per unit area). It is also of obvious advantage if these new tools can be used with existing robotic printers.

Although a number of strategies exist for fabricating microarrays based on pin printing methods, all current pins suffer from one or more of the following problems: [a] they do not yield feature sizes below 35 micrometers, [b] they cannot print all solvents, solutions, and/or mixtures; [c] they are difficult to fabricate; and [d] they are expensive to purchase.

We have developed a new two part pin system that can be easily retrofitted to existing robotic pin printers. The system consists of a metallic or polymeric pin mount and a tailored pin. With this system one can produce features that are on the order of 10 micrometers or less in diameter by using a standard robotic pin printer. The system also allows one to custom tailor the distal pin tip surface chemistry to allow the printing of a wide variety of solvents, solutions, and mixtures.

The present invention can be used to increase microarray density by 100-fold over standard methods and by 16-fold over the best methods in the literature.

Figure 12:
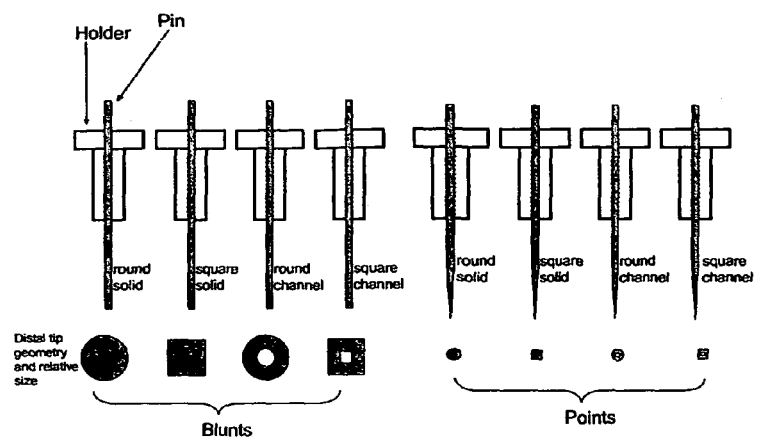
FIG. 12 is a schematic of the pin system along with eight possible pin types/geometries.
Figure 13:
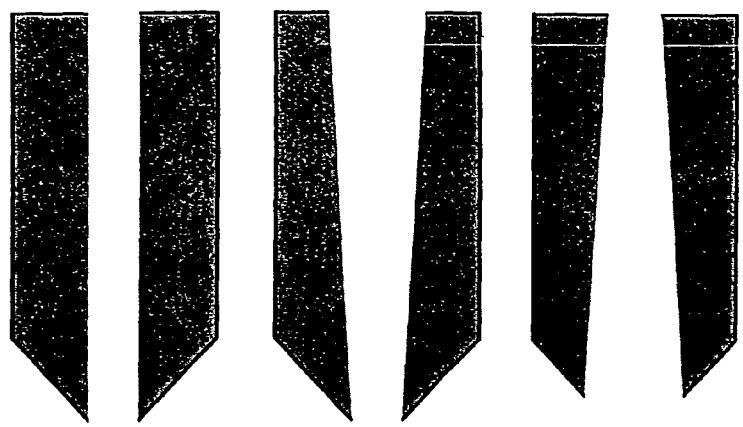
FIG. 13 represents potential geometries at the distal end of a channel-based pin.

A cross-sectional view of the invention is given in FIG. 12. The system consists of a metallic or polymeric pin holder and a tailored pin. In operation, the pin is inserted into the holder such that the distal pin end is directed toward the substrate onto which one wishes to form the microarray. The pin is then dipped into the solution to be printed. The solution wets the pin exterior (solid) or wets the pin exterior and fills the pin channel (channel) depending on the exact pin geometry one chooses (see FIGS. 12 and 13).

The pin is fabricated from non-metallic materials. Examples include optical fibers (solid), glass, quartz or organic and/or inorganic polymer precision rod (solids), or glass, quartz or organic and/or inorganic polymer capillaries (channels); materials that can be easily drawn after heating. The distal pin end is formed by cutting, etching, or pulling methods. The methods give blunt, point and point ends respectively.

Pins can be formed by a pulling process on a round or square rod and round or square tubing. A puller like a Warner model PMP-107/PMP-102 programmable pipette puller can be used for this task. In operation, the rod or tube is loaded into the puller where a point on the rod/tubing is brought to its softening point through the use of a heating device such as an electrical filament, laser or gas flame. Once the rod/tubing softening point temperature is reached, a mechanical parallel pulling force is applied to each end of the rod/tube and it is pulled to the desired tip diameter and profile. Depending on a number of preset variables (e.g., rob/tubing material, temperature, filament type and pulling force), numerous tip profiles and tip diameters can be fabricated. By using this technique tip sizes as small as 0.02 µm can be achieved. Pipette pullers can range in complexity from a simplistic spring/counter weight mechanical puller to highly sophisticated programmable microprocessor controlled pullers.

Once a micropipette has been pulled down to the desired tip diameter and taper, it can either be used as is or further processed. Processing is designed to change tip diameter, tip bevel, tip geometry, bending to various angles or to add (fuse) additional segments. To alter (increase) the tip diameter or to apply a bevel to the micropipette the tip is subjected to a controlled micro grinding process using a microbeveller. Microbeveller technology ranges from basic systems using wet alumina slurry on a rotating mirrored lapping disk, to sophisticated integrated optical-mechanical diamond based lapping wheel devices.

To reshape the pipette or to fuse the tip into a different geometry, a microforge system is used. A microforge uses a heating element, microscope, illumination, micromanipulators and microtools to change the shape of or contact fuse other elements to the micropipette pipette by heating certain sections of the micropipette to either soften (for bending) or melting (fusing) the micropipette. Some types of microforges can also fabricate metal and glass microtools.

The pin surface chemistry, the pin's geometry, the pin channel dimension, the pin distal end dimension, the pin velocity toward the substrate, and the pin's contact time to the substrate all effect the feature size and the ability to form features with a given solution on a given substrate (M. Schena in *Micorarray Analysis*, Wiley-Liss, 2003). The pin velocity and contact time are controlled by the robotic pin printer per se. The other factors are pin-dependent features that depend in large part on the pin's surface chemistry.

One of the difficulties in prior array printing systems is the inability to form extremely small sensors due to the failure of the tips to have chemical affinity for the sensor material. In the present invention, the pin surface chemistry can be easily controlled by [i] choosing specific materials from which to form the pins (glass, fused silica, organic polymers) that have intrinsically different surface chemistries and/or [ii] modifying the surface of a particular pin (exterior and/or interior) with one or more well-known surface derivitization or modification methods (e.g., silanization, plasma treatment, treatment with silicon alkoxides). The pins can be fabricated wherein the surface chemistry is formed as a gradient along the pin's long axis. In addition, the surface chemistry within the channel (gradient or not) can be different along the pin's long axis in comparison to the pin's exterior. In many cases, a pin's surface chemistry can be repeatedly changed.

An example of a reversible modification of the pin surface is the following based on a glass pin and aminopropyltri-methoxysilane (APTES, $(EtO)_3Si-(CH_2)_3-NH_2$). Here, a clean pin (HCl, NaOH wash) is immersed in a 3% solution of APTES in toluene. The pin and solution are allowed to react under ambient or reflux conditions for up to 48 h. The APTES reacts with the surface Si—OH residues on the glass pin to form siloxane bonds (Si—O—Si). After a toluene rinsing step, one is left with a pin surface that consists of $(Si-O)_3-Si-(CH_2)_3-NH_2$. The $Si-(CH_2)_3-NH_2$ residue can be readily removed by a simple acid/base washing step. The surface can then be remodified by using another organically modified silane or chlorosilane with one or more non-hydrolyzable (e.g., Si—C) residues.

An example of a permanent modification of the pin surface is the following based on a glass pin and trimethylchlorosilane (TMCS, $Cl-Si(Me)_3$). Here, a clean pin (HCl, NaOH wash) is immersed in a 3% solution of TMCS in toluene with 1-2% pyridine. The solution is refluxed for up to 24 h. The TMCS reacts with the surface Si—OH residues on the glass pin to form Si—O—Si bonds. The pyridine is used to capture the HCl that is produced in the reaction as a pyridine/HCl insoluble salt. After a toluene rinsing step, the pin surface consists of $Si-O-Si(Me)_3$ residues. These residues can also be hydrolyzed as described above for the APTES case, but the required conditions are more aggressive.

Once the pins are formed, they are grouped together in a pin printing apparatus. The pin printing apparatus can comprise pins which have similar or identical surface chemistries or geometries. However, the present invention also contemplates the use a pin printing apparatus of pins in a printer wherein the surface chemistry of each pin and/or its geometry are different. In this way, multiple solutions/samples with very different physicochemical properties can be printed simultaneously.

The instant embodiment allows smaller features within microarrays to be printed by using existing robotic pin printers. Pins can be formed with printing end bores in the range of from 0.02 to 100 microns which are capable of printing sensors in the range of from 0.02 to 100 microns This leads to a 16 fold improvement in feature density in comparison to the state-of-the-art and a 100-fold improvement over arrays formed with robotic pin printers and current commercial pins. The present invention makes possible the formation of microarrays having sensor densities of 1000 sensors per square millimeter and greater.

The present embodiment also provides a convenient way to reversibly tune the surface chemistries at or within the pin to fine tune the printing. The current embodiment provides a convenient way to print circular and square features. The current embodiment allows for simultaneous printing with pins having different surface chemistries, allowing the simultaneous printing of different solutions.

The present invention also provides diversified xerogel-based sensors which can conveniently be used with the photonic sensor system of the present invention to improved detection and quantification of analytes.

Traditional sensing methods have focused on the development of single sensors for a given target analyte. Sensor array technology has helped to improve on this situation by opening the door to the parallel detection of multiple analytes in a sample. However, individual sensor elements within an array are generally designed for a specific analyte. Thus, the single analyte-single sensor approach, despite parallel detection schema, remains a fixture in modern chemical sensing.

A persistent problem with the single sensor-single analyte approach is that in order to ensure accurate results and determine false readings one must include frequent recalibration and sensor testing steps in order to ensure that accuracy and sensitivity to the analyte has not declined.

The diversified analyte detection embodiment of the present invention has significant advantages in that it improves overall sensor accuracy, minimizes the need for recalibration and makes possible the clear identification of false readings from failing sensor elements.

The diversified sensor embodiment of the present invention provides for the use of multiple different photonic sensors in a single photonic array, each sensor being designed to give a different response to a target analyte (e.g, $O_2$). By "different response," it is meant that each of the sensors has a different sensor response curve. A "sensor response curve" is the relation between sensor response (i.e., reduction or increase in emission from the sensor upon exposure to given concentration of analyte) and analyte concentration. The information from multiple sensor response curves is used to detect and quantify a given target analyte in a sample.

A non-limiting illustration of the diversified sensor embodiment of the present invention is the detection of a specific target analyte, $O_2$, with xerogel based sensors. The specific detection method is based on quenching of a luminescent molecule in the sensor by $O_2$.

The sensing of $O_2$ is a non-limiting example. The invention is amenable to other analytes and other sensing methods. Particularly convenient are methods that can be performed within a xerogel-based sensor platform. For example, other sensing strategies which can be employed in the context of the diversified sensors embodiment include, for example, sensors based on organic polymers, biosensors, sensors based on inorganic polymers, sensors based on molecular imprinting and nanoimprinting, sensors based on molecular recognition or biomimetic strategies, sensors based on intermolecular interactions of any type (e.g., collisional, electron transfer, energy transfer. The use of the diversified sensors embodiment of the present invention in the sensing of $O_2$ is described in Example 3.

In order to have a sensor system which can indicate in a single measurement that at least one of the sensors in a sensor array system is failing, the sensor array should include at least two different types of sensors. When the two types no longer give the same reading when exposed to the same sample (i.e., substantially identical concentrations of analyte), it can be determined that at least one type of sensor has failed. In order to know in a single measurement which type of sensor has failed, it is preferable to include no less than three different types of sensors in the sensor array. If it is determined that one type of sensor gives a response which is inconsistent with the responses of the remaining types of sensors when exposed to the same sample (i.e., substantially identical concentrations of analyte), the sensors of that type can be replaced, or their readings can be disregarded. By "consistent response," it is meant that for a given sensor type, the response corresponds to an analyte concentration which is consistent with the concentrations indicated by the other sensor types.

In another embodiment, the diversified sensors method of the present invention can be used to detect multiple analytes, as long as the sensor array bears at least two different types of sensor corresponding to each analyte. In yet other embodiments, the sensors are not arranged in an array, but are in other arrangements, such as multilayer architectures, continuums, gradients or combinations of these. For example, the diversified sensors embodiment can also be used to improve the accuracy of concentration measurement in imaging applications which measure the spatial variation of an analyte concentration. However, if the diversified sensors embodiment is included in an imaging context, care should be taken to ensure that any differences in concentration registered by different types of sensors which are being compared for accuracy purposes are not entirely due to spatial variations in analyte concentration.

In yet another embodiment, the present invention provides high stability Xerogel-based $O_2$ sensors with linear calibration curves. These novel sensors exhibit excellent selectivity and sensitivity. Additionally, the sensors have detection limits as low as 1 pg/mL they are easy to calibrate, and they can be stable for periods at least as long as 12 months, and often as long as several years.

In the chemical sensing literature, $O_2$ is a common target analyte because it is important in biological, environmental, industrial applications. $O_2$ is traditionally quantified by using Clarke electrode (CE); however, the CE consumes $O_2$ and it can be poisoned by sample constituents (e.g., $H_2S$, proteins, certain anesthetics). Given these limitations, researchers have expended substantial effort to develop optically based $O_2$ sensors. The most common of these sensors exploit the well-known effects of $O_2$ quenching on the intensity (1) or excited-state lifetime ($\tau$) of an immobilized luminophore (fluorophore or phosphore) as described in Eqn. 1.

$$\frac{I_0}{I} = \frac{\tau_0}{\tau} = 1 + K_{SV}[Q] = 1 + k_q \tau_0 [Q] \quad (1)$$

When luminophores are immobilized, as they are in most available types of chemical sensors, Eqn 1 is generally not obeyed, and the Stern-Volmer plots for these systems are nonlinear. While the degree of nonlinearity depends on a wide variety of factors, the nonlinearity in every case is associated with the luminophore molecules being distributed between two or more different types of environment which each of which cause the luminophore to exhibit different kq or $\tau_0$ values.

Because the Stern-Volmer plots are nonlinear, currently available sensors require that one calibrate the sensor using multiple standards (i.e., multipoint calibration). The more non-linear the Stern-Volmer plot, the more the greater the number of standards that are needed to accurately define the calibration/working curve. Linear Stern-Volmer plots do not require such elaborate standardization/calibration. In addition, in some cases, the sensor response is not stable over time. Thus both the multipoint calibration requirement and drift problems can frustrate the development of a reliable sensor platform.

Over the years, many methods have been described to immobilize sensor chemistries for sensor development. These methods include physisorption. covalent attachment, and entrapment/sequestration. Physisorption methods are the most simple; however, several disadvantages exist. Random orientation of the sensing chemistry on the substrate can lead to target analyte inaccessibility or distributions of accessibilities. In addition, because this method lacks covalent chemical bonds, the "immobilized" sensing chemistry often leaches/desorbs, causing drift problems. Certain lifetime-based sensor strategies can address some of these issues, but these approaches require more costly and complex instrumentation. Covalent attachment strategies eliminate the leaching problem; however, they are chemically more complex, they tend to be more time-consuming and costly to use. Furthermore, due to surface reorganization, denaturation of protein-based sensing chemistries, or both, they do not guarantee full accessibility or absence of drift.

Sequestration of the recognition chemistry within a porous, three-dimensional network has become an attractive means to immobilize sensing chemistries. Sol-gel processing methods have been used to alleviate several of the aforementioned immobilization problems. There have been a significant number of luminescence-based $O_2$ sensors reported in the literature based on sol-gel-derived materials. However, a common feature of previous sol-gel-derived $O_2$ sensors is that the Stern-Volmer plots are non-linear, necessitating multipoint calibration; the sensor response is not stable over the long term; or both. Additionally, the surface structure of many of these sol-gel-derived sensors is often cracked The cracked surfaces often flake off or the sensor response is neither stable nor reliable.

In this embodiment of the present invention, a series of luminophore-doped xerogels composed of n-octyltriethoxysilane (Octyl-triEOS) and tetraethoxysilane (TEOS) are provided. The luminophore is tris (4,7-diphenyl-1,10-phenanthroline}ruthenium(II) ([Ru(dpp)$_3$]$^{2+}$) and the target analyte is $O_2$. Results show that these composite xerogels can be tailored to produce uniformly composed sensors that exhibit high sensitivity, long-term stability, and linear response curves, and a resistance to cracking.

The sensor materials of the present embodiment have an Octyl-triEOS content in the range of from 0 to 50 mole %, a TEOS content in the range of from 50 to 100% mole % and a [Ru(dpp)$_3$]$^{2+}$ content in the range of from 1-1000 ppm. Other xerogel formulations and compositions can be used to tailor the sensitivity and selectivity of the sensors.

In an additional embodiment, the present invention provides a method of irradiating a sensor having a non-linear Stern-Volmer plot (multiple luminophores, multiple luminophore environments, or both), such that the sensor emits radiation which, upon analysis, gives the same information given by a diversified group of sensors, each sensor containing a single luminophore in a single environment (i.e., each sensor having a linear SV plot).

We describe a method that uses a single luminescence-based sensor, a modulated excitation source, and phase-sensitive detection to produce a wide variety of response profiles from a single sensor. That is, we can create response profile diversity from a single sensor. The method is derived and described as follows.

In a luminescence-based quenchometric sensor with one luminophore distributed so that each luminescent molecule encounters an identical microenvironment, one can write the sensor's response as:

$$I_o/I = \tau_o/\tau = 1 + K_{SV}[Q] = 1 + k\tau_o[Q] \tag{1}$$

In this expression, $I_o$ is the intensity from the sensor in the absence of quencher, Q; I is the intensity in the presence of quencher Q; $\tau_o$ is the excited-state luminophore lifetime in the absence of Q; $\tau$ is the excited-state luminophore lifetime in the presence of Q; $K_{SV}$ is the Stern-Volmer constant; [Q] is the concentration of quencher; and k is the bimolecular quenching constant the describes the encounters between Q and the luminophore. Under these conditions, a plot of $I_o/I$ vs. [Q] will be linear with a slope of $K_{SV}$. To tune $K_{SV}$ (i.e., create diversity) requires that one adjust k and/or $\tau_o$, making a new sensor element.

Consider a second quenchometric sensor element of similar design to the one described above, but with two different luminophores (A and B) that each responds to a different degree to Q. Consider also that these luminophores possess unique excited-state luminescence lifetimes in the absence of Q (i.e., $\tau_{o,A}$ and $\tau_{o,B}$).

Under steady-state detection conditions one can write this sensor's response as:

$$I_o/I = \langle\tau_o\rangle/\langle\tau\rangle = [(L_A/(1+K_{SV,A}[Q])) + [(L_B/(1+K_{SV,B}[Q]))] \tag{2}$$

In this expression, $I_o$, I, and [Q] are defined above; $\langle \rangle$ denotes the weighted mean excited-state luminescence lifetimes; $K_{SV,A}$ and $K_{SV,B}$ are the Stern-Volmer constants associated with luminophore A and B, respectively; and $L_A$ and $L_B$ are the fractions of the total luminescence arising from luminophore A and B, respectively. In addition, one can write:

$$K_{SV,A} = k_A \tau_{o,A} \tag{3a}$$

$$K_{SV,B} = k_B \tau_{o,B} \tag{3b}$$

where $k_A$ and $k_B$ represent the bimolecular quenching constants for luminophore A and B, respectively. Under these conditions, a plot of $I_o/I$ vs. [Q] will be non-linear and curve toward the Q axis. To tune this type of sensor's response (i.e., to create diversity) requires that one adjust $k_A$, $\tau_{o,A}$, $k_B$, $\tau_{o,B}$, $L_A$ and/or $L_B$, making a new sensor element.

The aforementioned cases can be extended to N luminophores. In all cases that use steady-state detection methods, the generation of sensor response diversity requires that one adjust some aspect of the sensor (vide supra) and fabricate additional sensors.

If we reconsider the A and B containing sensor element that we just described and we now excite the sensor with sinusoidally modulated light at frequency (f), we see that the resulting luminescence will be phase shifted (θ) and demodulated (M) to an extent that depends on the luminophore excited-state fluorescence lifetimes and their relative contributions to the total emission. Specifically, for luminophores A and B we can write:

$$\theta_A = \arctan(2\pi f \tau_A) \tag{4a}$$

$$\theta_B = \arctan(2\pi f \tau_B) \tag{4b}$$

$$M_A = [1 + (2\pi f)^2 \tau_A^2]^{-1/2} \tag{5a}$$

$$M_B = [1 + (2\pi f)^2 \tau_B^2]^{-1/2} \tag{5b}$$

We can also write, at any quencher concentration:

$$L_A(Q) = F_{A,o}(1 + (k_A \tau_{o,A}[Q]))^{-1} \tag{6a}$$

$$L_B(Q) = F_{B,o}(1 + (k_B \tau_{o,B}[Q]))^{-1} \tag{6b}$$

$$\tau_A(Q) = (1/\tau_{o,A} + k_A[Q])^{-1} \tag{7a}$$

$$\tau_B(Q) = (1/\tau_{o,B} + k_B[Q])^{-1} \tag{7b}$$

If we record the luminescence from a sensor that contains two luminophores (A and B) with a phase-sensitive detector (e.g., a lock-in amplifier), we can write the generalized phase-sensitive luminescence signal (PSLS) as:

$$PSLS(\theta_D) = L_A M_A \cos(\theta_D - \theta_A) + L_B M_B \cos(\theta_D - \theta_B) \tag{8}$$

In this expression, $L_A$ and $L_B$ denote the fraction of the total luminescence signal that arises from luminophores A and B, respectively; $M_A$ and $M_B$ represent the demodulation factors associated with luminophores A and B, respectively; $\theta_D$ is the detector (i.e., lock-in amplifier) phase angle; and $\theta_A$ and $\theta_B$ are the phase angles for luminophores A and B, respectively.

If we now use Eqns. 4-7 and substitute them accordingly into Eqn. 8, we can write an expression for the phase-sensitive analog of Eqn. 2, namely:

$$PSLS_o(\theta_D,0)/PSLS(\theta_D,Q) = [L_{o,A}M_{o,A}\cos(\theta_D-\theta_{o,A}) + L_{o,B}M_{o,B}\cos(\theta_D-\theta_{o,B})]/[L_A(Q)M_A(Q)\cos(\theta_D-\theta_A(Q)) + L_B(Q)M_B(Q)\cos(\theta_D-\theta_B(Q))] \quad (9)$$

Eqn. 9 provides the key relationship between the fundamental properties of the sensor element (i.e., $k_A$, $\tau_{o,A}$, $k_B$, $\tau_{o,B}$, $\tau_{o,A}$ and/or $L_{o,B}$) and the phase-sensitive analog of $I_o/I$ (i.e., $PSLS_o/PSLS$) as a function of [Q], $\theta_D$ and f.

Figure 25:
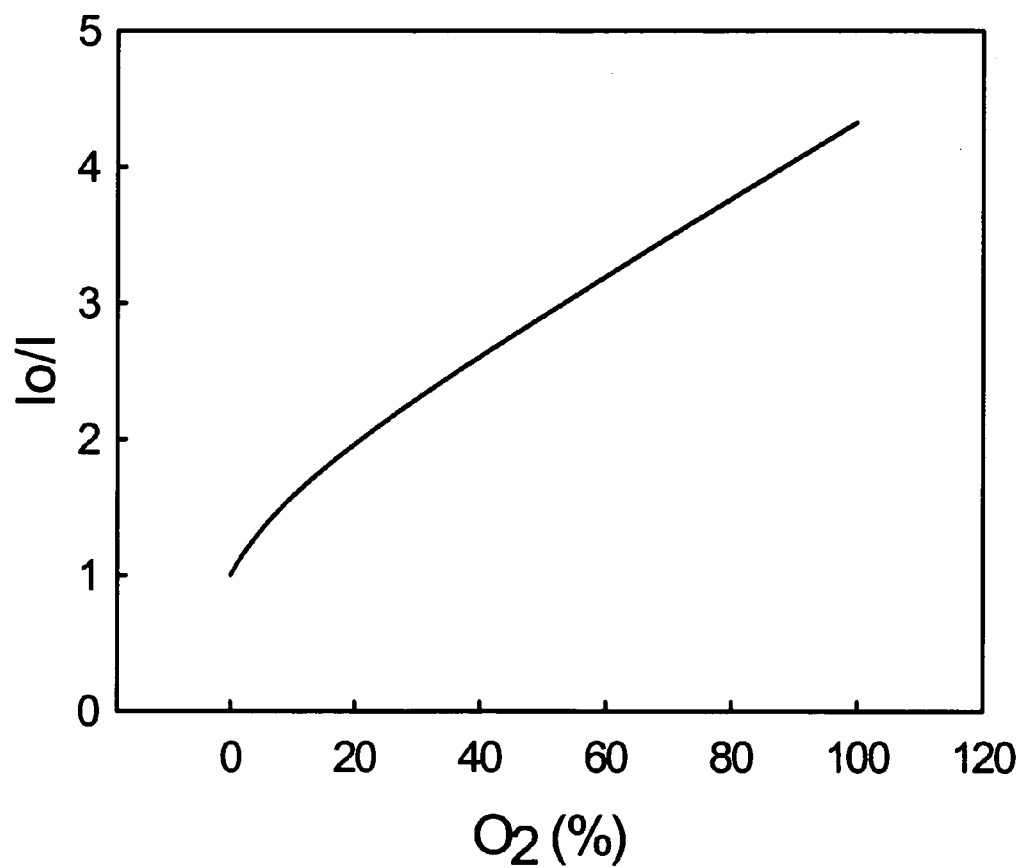
FIG. 25 is a simulated $i_o/i$ vs. [q] plot for a sensor element that contains two luminophores with excited-state lifetimes of 5000 ns and 500 ns.
Figure 26:
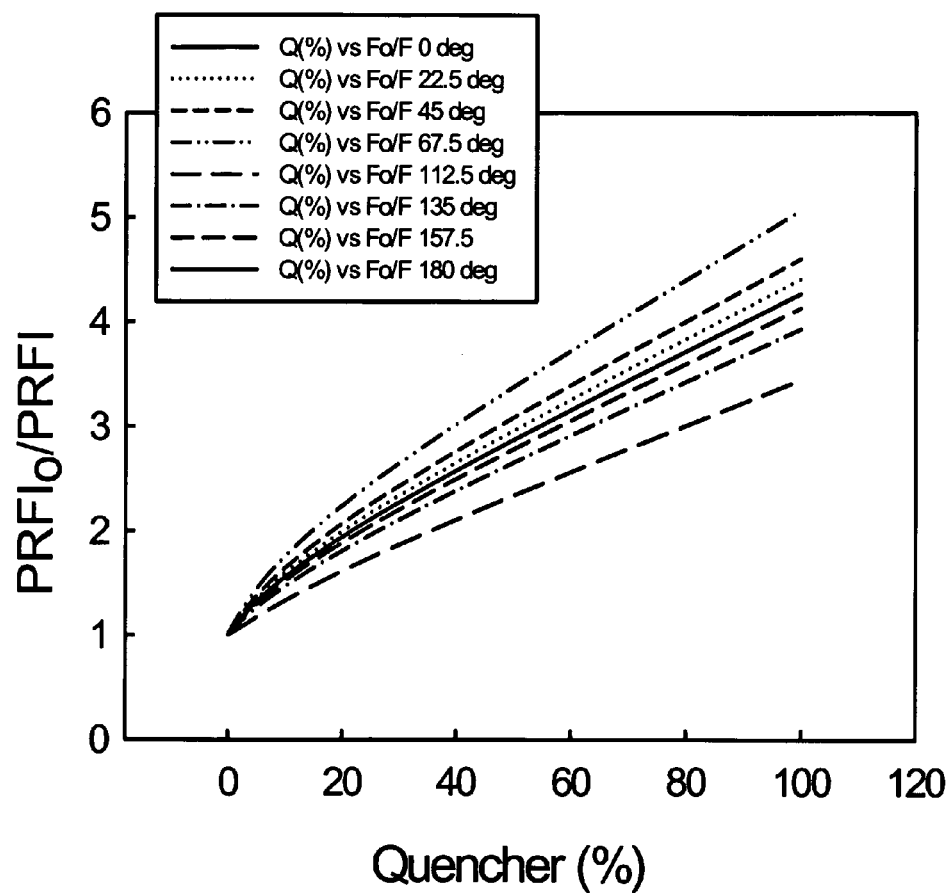
FIGS. 26-31 show results from a series of simulations based on the same sensor element.
Figure 27:
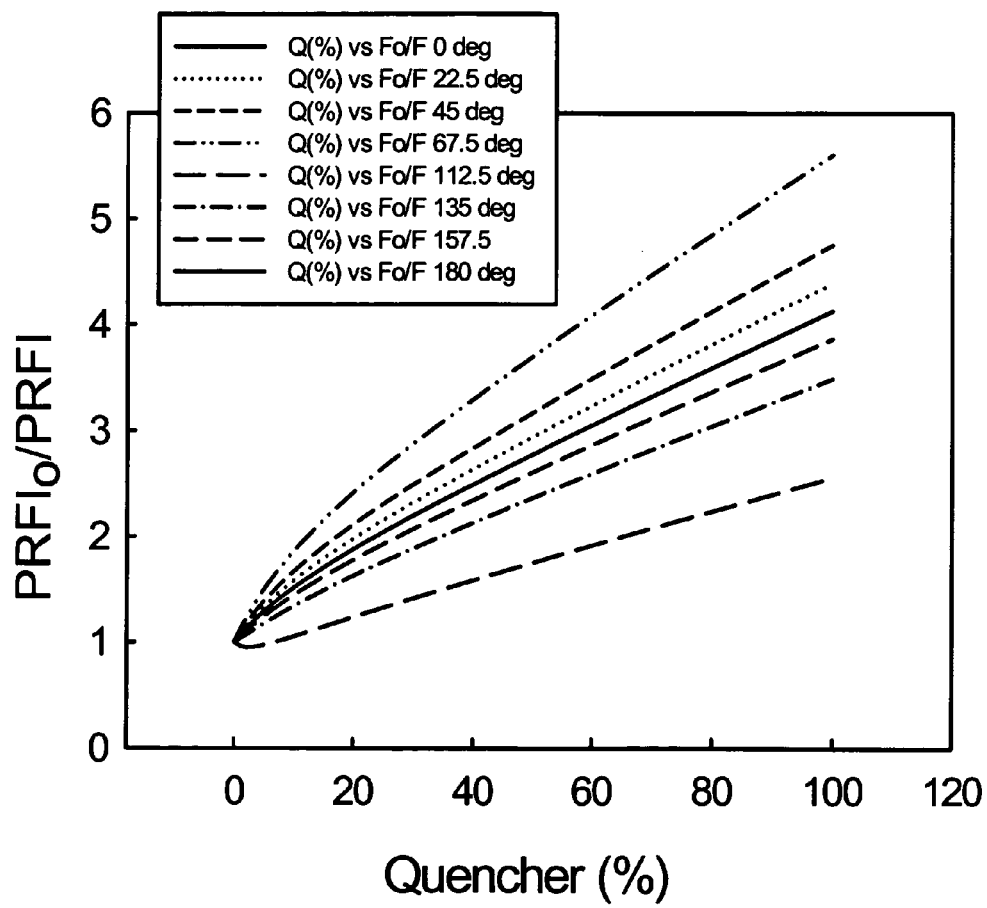
Figure 28:
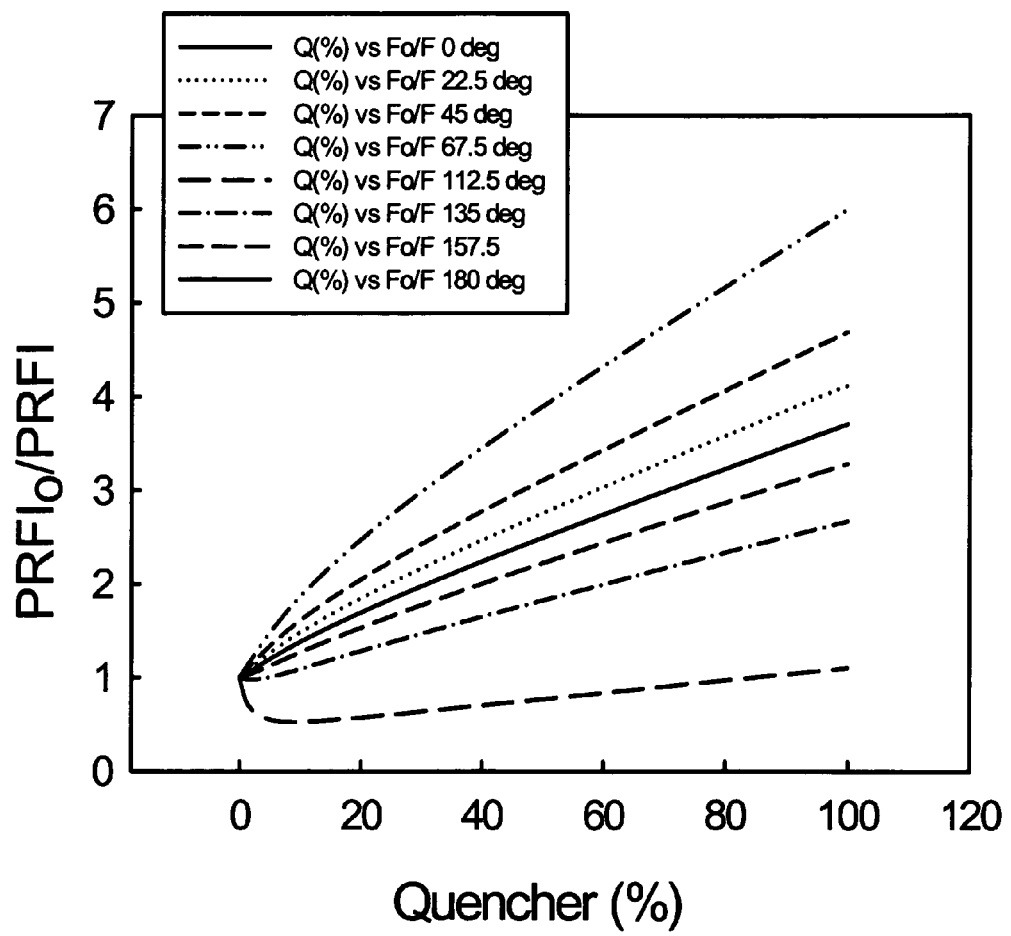
Figure 29:
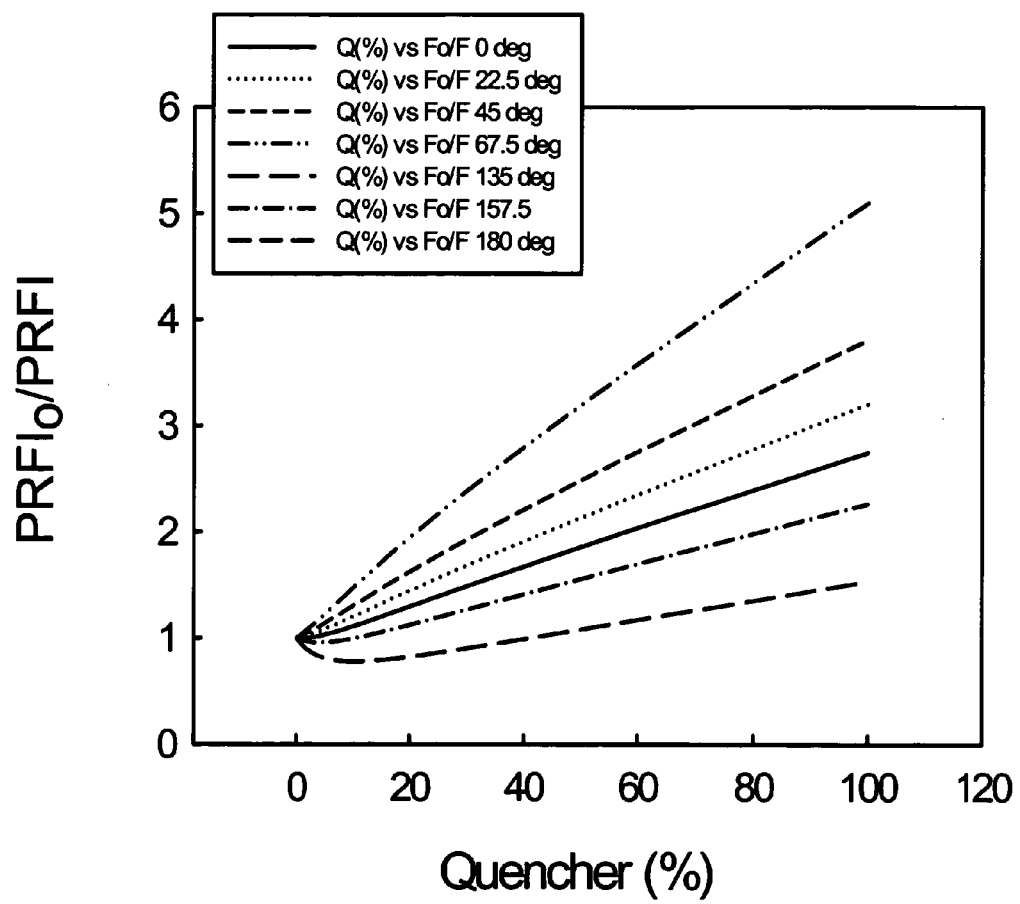
Figure 30:
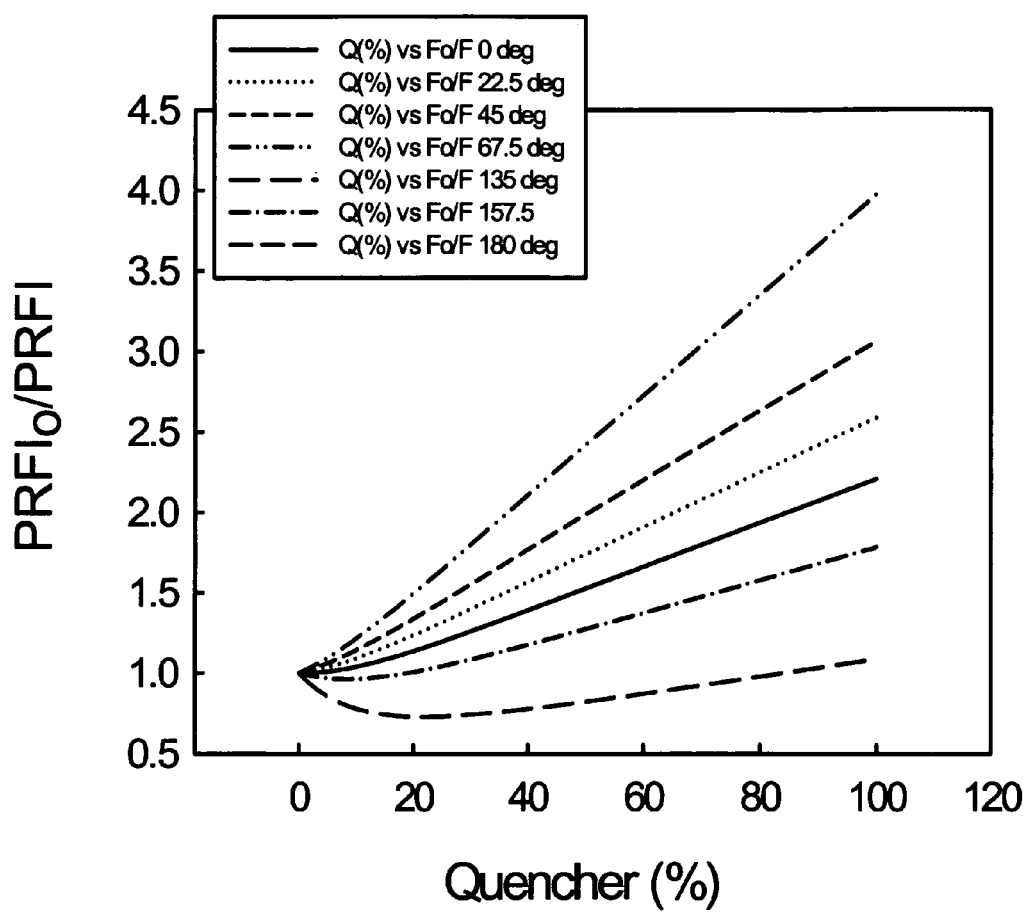
Figure 31:
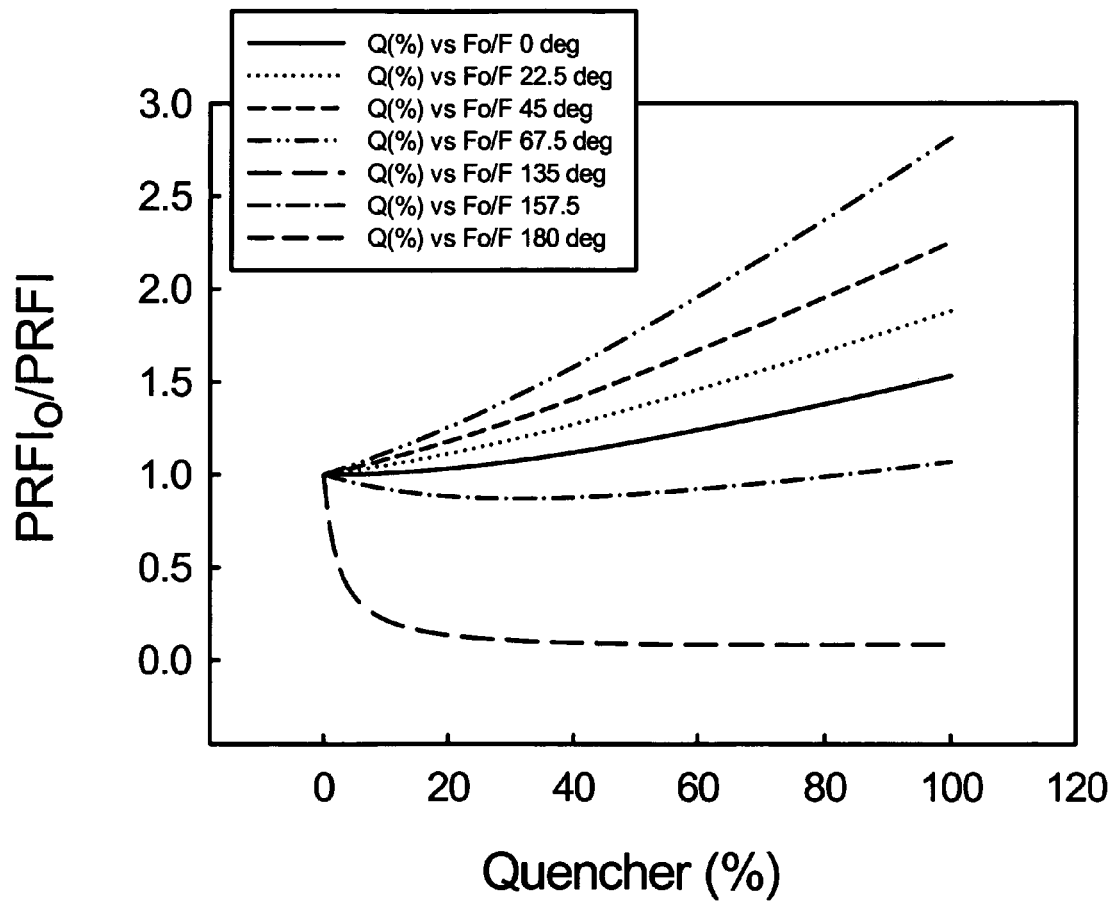

FIG. 25 presents the simulated $I_o/I$ vs. [Q] plot for a sensor element that contains two luminophores with excited-state lifetimes of 5000 ns and 500 ns ($\tau_{o,A}$, and $\tau_{o,B}$, respectively) as a function of added $O_2$ (0-100%), the quencher, with $L_A$ $L_B$, and $k_A=k_B=3\times10^6$ $(O_2\%)^{-1}$. The response curve is non-linear. Diversification is possible here only by changing $k_A$, $\tau_{o,A}$, $k_B$, $\tau_{o,B}$, $L_A$ and/or $L_B$, making a new sensor element and corresponding response profile.

Figure 4:
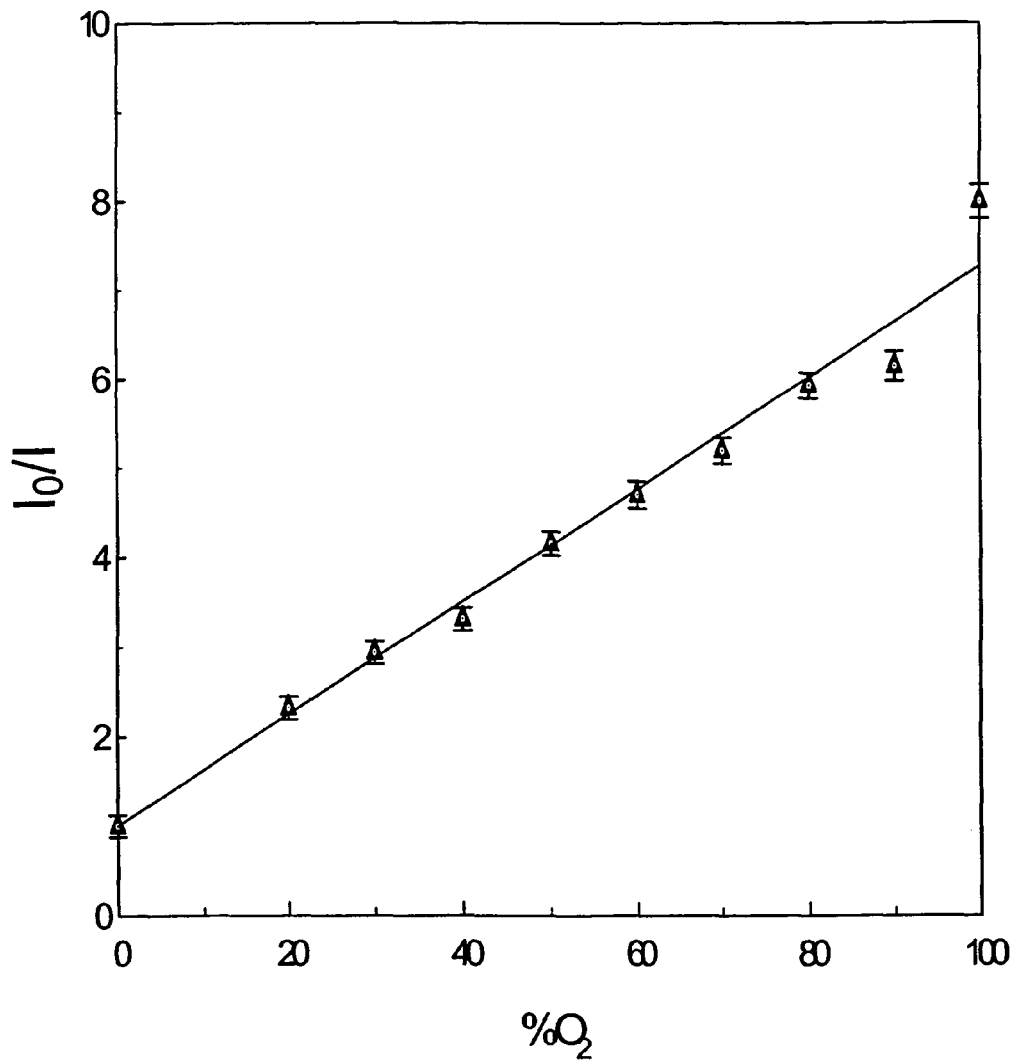
FIG. 4 is a typical calibration curve for an $O_2$ responsive sensor element excited by the combination of a 2 mCi$^{90}$Sr beta emitter and an EJ-200 scintillator.

FIGS. 26-31 present partial results from a series of simulations based on the same sensor element described in FIG. 1 when the sensor element is excited with sinusoidally modulated light and the luminescence is recorded by phase-sensitive detection. The simulations were performed as a function of [Q], $\theta_D$ and f. FIG. 2 presents the simulation when f=5 kHz. FIG. 3 presents the simulation when f=10 kHz. FIG. 4 presents the simulation when f=20 kHz. FIG. 5 presents the simulation when f=50 kHz. FIG. 6 presents the simulation when f=100 kHz. FIG. 7 presents the simulation when f=250 kHz. Inspection of these results shows a number of interesting trends. First, the response profiles depend on $\theta_D$. Second, the response profiles depend on f. These results are to be contrasted with the response profile under steady-state conditions (FIG. 25) which is singular. Thirdly, there are conditions where the phase-sensitive response profiles exhibit negative excursions. This is an additional unique aspect of our phase-sensitive detection modality that is not observed in a steady-state measurement. Together these simulations argue for a new strategy to produce massive sensor response diversity with only a single sensor element.

Figure 32:
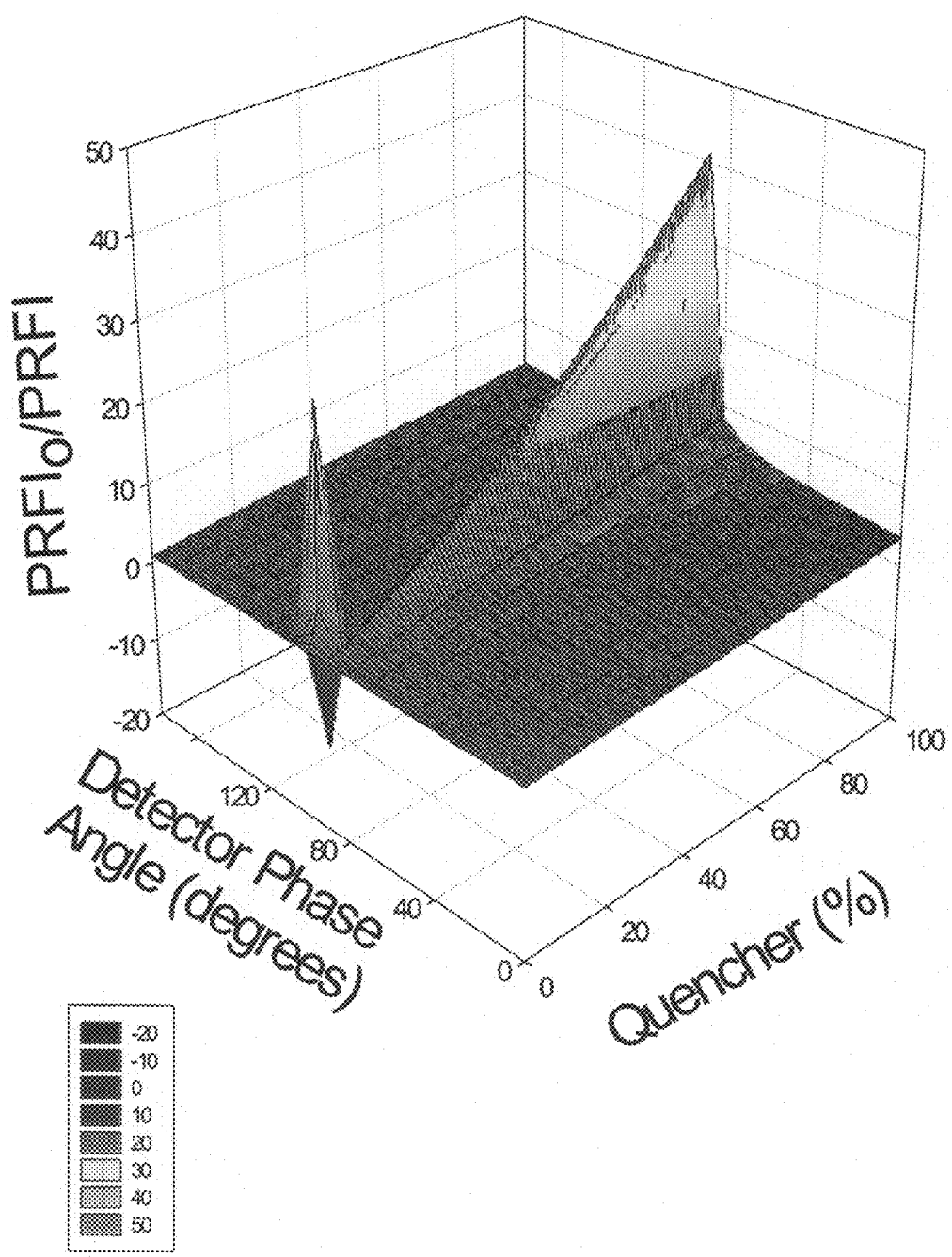
FIGS. 32-34 show three-dimensional simulations for the sensor element of FIG. 25.
Figure 33:
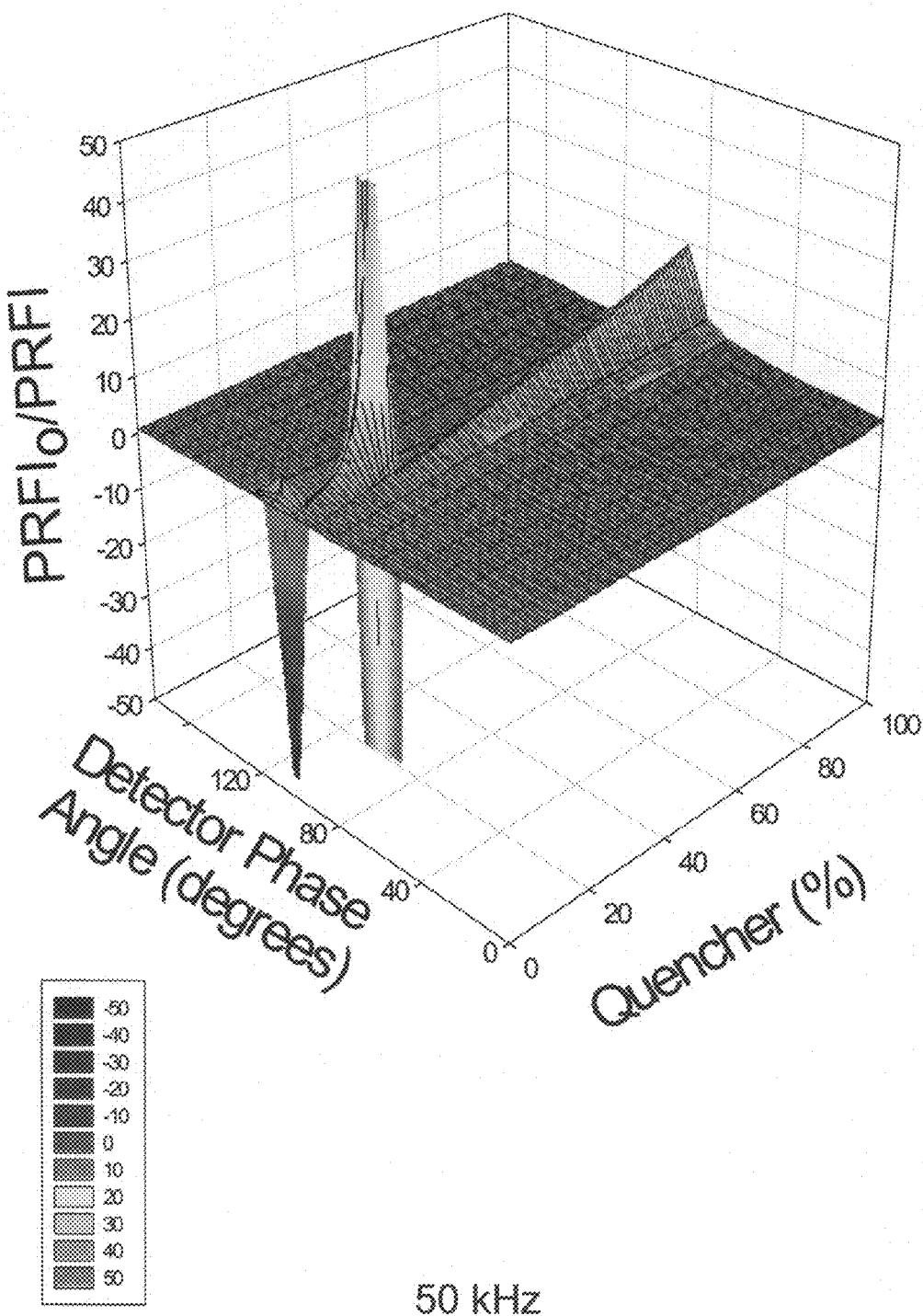
Figure 34:
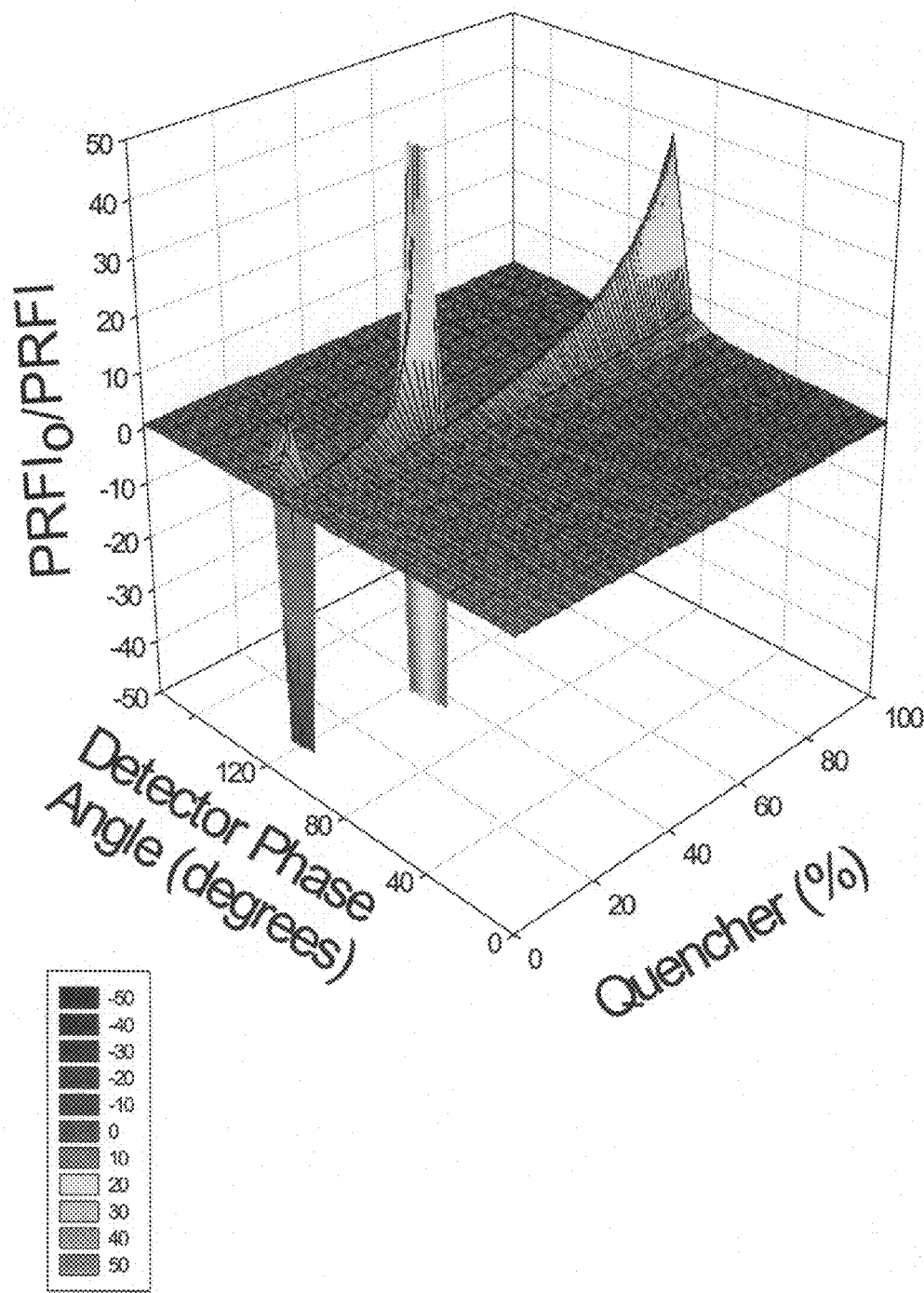

FIGS. 32-34 present the full 3-D simulations for the sensor element discussed above at 20 kHz (FIG. 32), 50 kHz (FIG. 33), and 150 kHz (FIG. 34). Inspection of these results echo the trends described in the partial simulations (i.e., FIGS. 26-31) and they show that there are specific values of $\theta_D$ and f that produce hyper-sensitive responses that significantly exceed the sensitivity of the same sensor used in a steady-state detection mode. Note too that there are cases where very large negative values of $PSLS_o/PSLS$ are indicated; steady-state measurements yield only positive values of $I_o/I$. Finally, notice that the general shape of the response curves change significantly depending on $\theta_D$ and f. Together, theses results argue for a completely new way to create diversity in chemical sensing without the need to diversify the sensors themselves.

Figure 35:
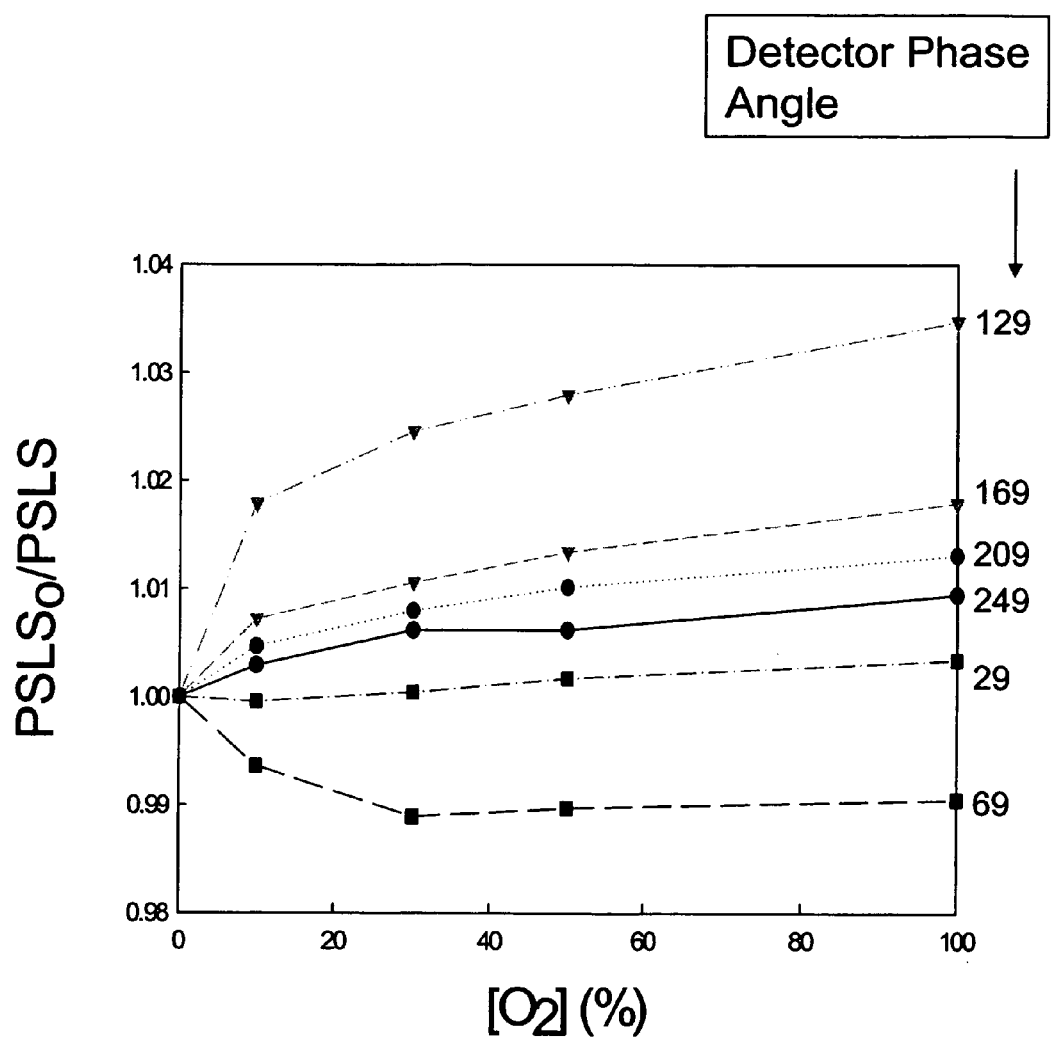
FIG. 35 shows use of a sensor element containing a xerogel doped with $[Ru(dpp)_3]^{2+}$ and $[Ru(bpy)_3]^{2+}$ and excited with 450 nm light that is modulated at 20 kHz.

FIG. 35 presents a portion of an experiment using a sensor element composed of a sol-gel-derived xerogel that we doped with two luminophores ([Ru(dpp)$_3$]$^{2+}$ and [Ru(bpy)$_3$]$^{2+}$). In this experiment the sensor element is excited with 450 nm light that is modulated at 20 kHz. The emission is passed through an optical filter and detected by a photodiode. The photodiode output is directed to a lock-in amplifier and the PSLS is detected as a function of detector phase angle. These curves are unique and they exhibit most of the features seen in our simulations (FIGS. 26-34).

Example 1

Figure 10:
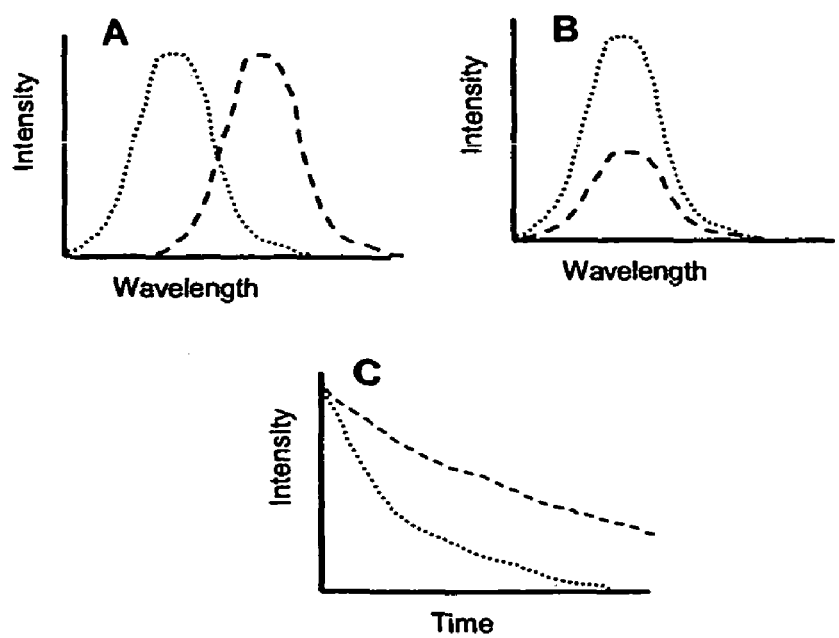
FIG. 10 is a depiction of exemplary changes in sensor response upon exposure of the sensor to an analyte. A) shift in emission; b) decrease in intensity of emission; c) change in emission lifetime.
Figure 11:
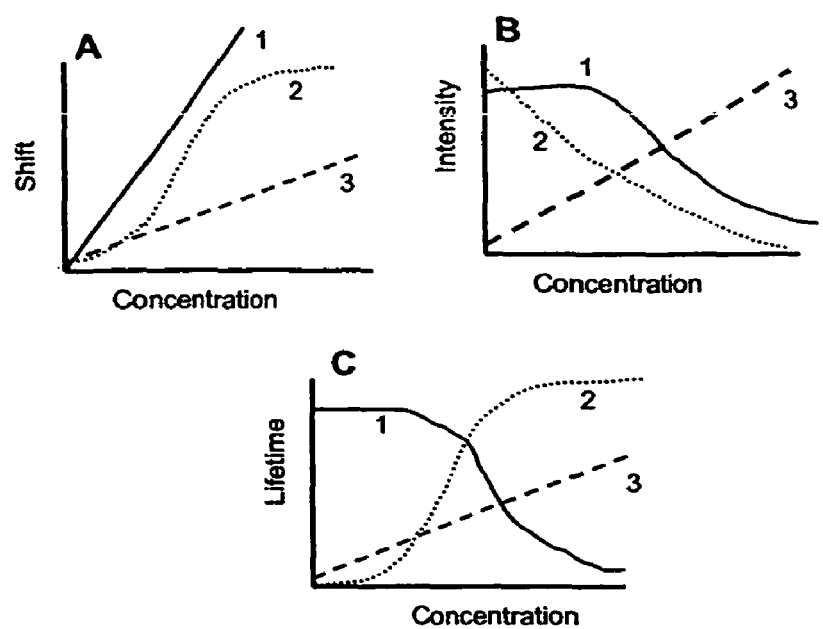
FIG. 11 is a diversification of sensors. A) examples of different sensing chemistries/sensing layer formulations for the same target analyte; 11b) examples of calibration curves 1-3 representing different sensing chemistries/sensing layer formulations for the same target analyte. Potential calibration curves are presented in FIG. 11c.

The unique nature of the beta emission yields several possible data formats from the CRNILS (FIG. 10). In FIG. 10A, results are presented where the luminescence spectrum from the sensing layer shifts in the presence of the target analyte. Potential calibration curves are presented in FIG. 11A. Curves 1-3 in FIG. 11A represent different sensing chemistries/sensing layer formulations for the same target analyte-diversification. In FIG. 10B, results are presented where the luminescence intensity from the sensing layer changes in the presence of the target analyte. Potential calibration curves are presented in FIG. 11B. Curves 1-3 in FIG. 11B represent different sensing chemistries/sensing layer formulations for the same target analyte-diversification. In FIG. 10C, results are presented where the time-resolved intensity decay profiles of the sensing layer change in the presence of the target analyte. Potential calibration curves are presented in FIG. 11C. Curves 1-3 in FIG. 11C represent different sensing chemistries/sensing layer formulations for the same target analyte diversification. The sensing modalities presented in FIGS. 10 and 11 can be used independently or together. One particularly attractive aspect of these detection modalities arises because excited-state lifetimes are independent of the luminophore concentration. Therefore, if there were some level of photobleaching, decrease in source output, etc., it would not present a problem. Further, such lifetime-based sensing strategies simplify calibration.)

Example 2

Figure 14:
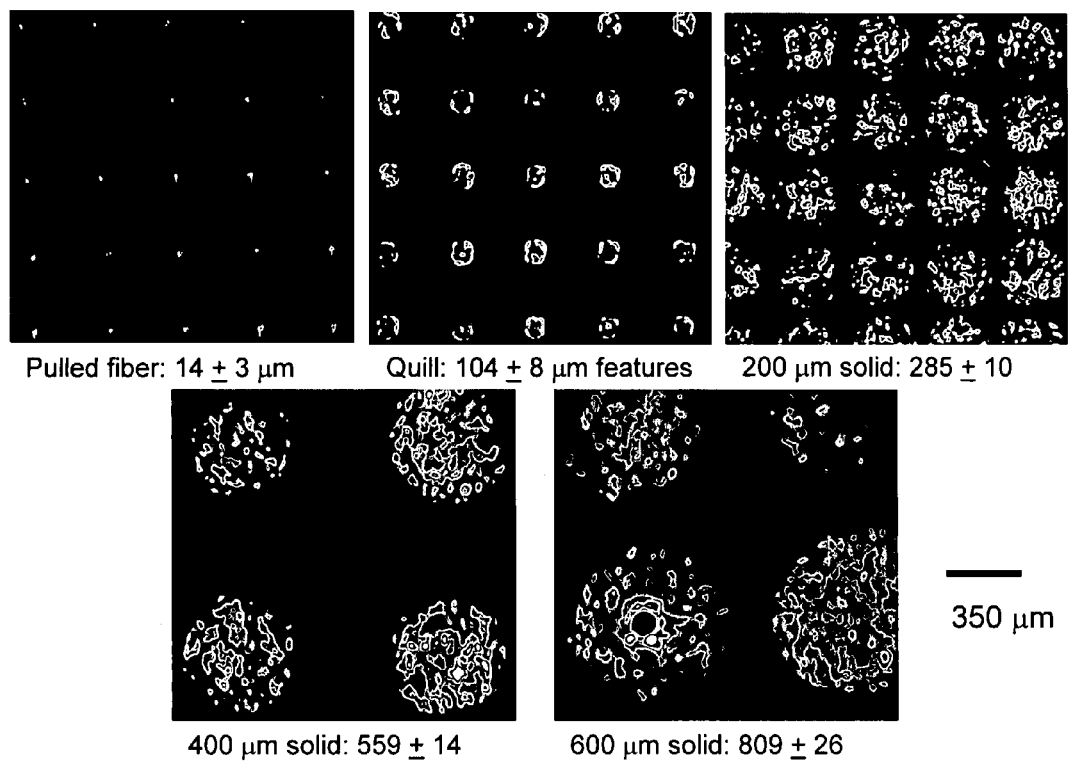
FIG. 14 represents examples of pin printed microarrays formed with the new pins compared to quill, and 200, 400 and 600 µm solid pins. Feature sizes are shown.

FIG. 14 presents examples of pin printed microarrays that have been formed in the laboratory. The printing solution was a 50:50 mole % tetramethylorthosilane:n-octyl-trimethoxysilane-based xerogel doped with the fluorophore rhodamine 6G.

The arrays are illuminated with a laser in an epi-fluorescence geometry, detection is with a CCD camera. The "Pulled fiber" array was formed from a single fused silica optical fiber (geometry, round, solid, points in FIG. 12). The printed feature sizes are 14±3 micrometers in diameter. Arrays are also shown for commercial quill and solid pins. In all cases, the feature size with the commercial pins is at least an order-of-magnitude larger in diameter when compared to our "Pulled fiber". The pulled fiber can be used to increase the printed element density by ~100x).

Example 3

Inspection of Eqn. 1 reveals two strategies for tuning the sensitivity of any quenchometric sensor—adjust $\tau_0$ and/or adjust kq. (Note; In other sensor schemes one might tune the binding affinity, partition coefficient, etc. to generate the necessary sensor diversity.)

To illustrate the potential of this tuning we formed a diversified library of xerogel-based sensor elements for $O_2$. Here, each sensor element is designed so that it exhibits a distinct calibration curve and/or response time course to dissolved or gaseous O2. In this particular example, these diversified xerogel-based photonic sensor libraries are derived from luminophore-doped xerogels. The xerogels are composed of n-alkyl ($C_1$-$C_{12}$)-triethoxysilane ($C_1$-$C_{12}$)-TriEOS) and tetraethoxysilane (TEOS) or n-alkyl ($C_1$-$C_{12}$)-trimethoxysilane ($C_1$-$C_{12}$)-TriMOS) and tetramethyoxysilane (TMOS) precursors. The luminophores are tris(4,7-diphenyl-1,10-phenanthroline)ruthenium(ll), [Ru(dpp)$_3$]$^{2+}$ and/or tris(2,2'-bipyridyl)ruthenium(II), (Ru(bpy)$_3$]$^{2+}$ By using these precursors and luminophores we adjust $\tau_0$ and kq at will to produce collections of sensors for the same target analyte with unique responses (i.e., diversification).

Other xerogel precursors and luminophores can be used to further tune the sensor's analytical figures of merit beyond the ranges presented here. Secondary dopants (e.g. oligomers, polymer, surfactants, lipids, organically modified silanes) can also be added to the xerogel to effect further diversity. Other detection and molecular recognition schemes (e.g., molecular imprinting, nanoimprinting, SSTTX, PIXIES, affinity, protein-ligand, protein-protein, hybridization) can also be used.

Figure 15:
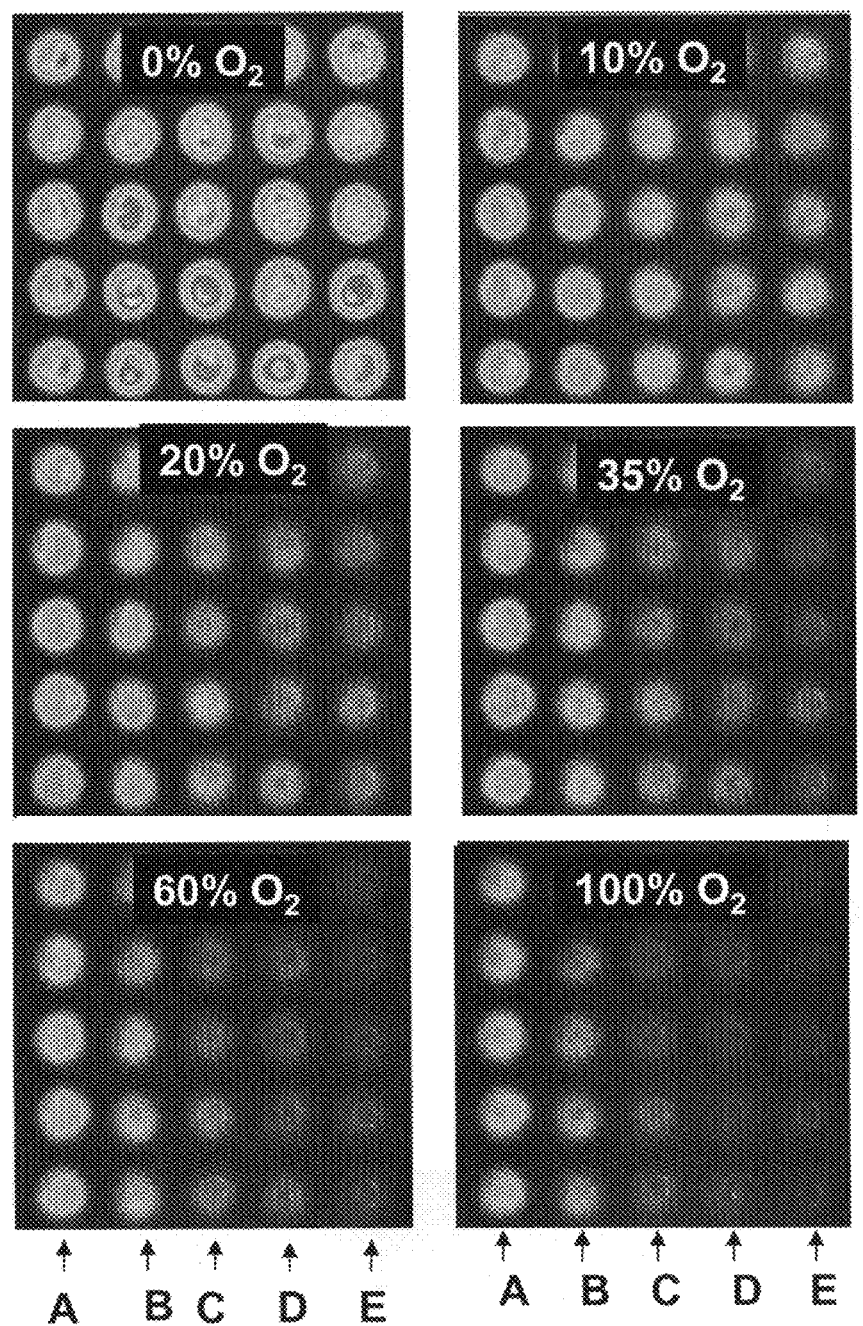
FIG. 15 shows a portion of a diversified, xerogel-based sensor library. The xerogel composites are identical. Sensors a-e contain different molar ratios of the dpp and bpy-based luminophores. This is an example of $\tau_o$-based diversification. The sensor element feature size is ~100 µm in diameter.

FIG. 15 presents a series of false color images from a small segment of a diversified xerogel-based $O_2$ responsive sensor library as a function of the gaseous $O_2$ concentration. This library is illuminated with an external laser and the emission from the individual sensor elements is detected by a charge coupled device detector. [Note: Other excitation/detection approaches are also possible]. The individual panels show the $O_2$-dependent response from a 25 element, diversified sensor library. Each column (labeled Sensors A-E) represents one of five sensor types. The five elements within each column represent replicates of a given sensor type. The individual sensor types were fabricated from a binary xerogel that is composed of identical molar ratios of TEOS and $C_8$-TriEOS precursors doped with different molar ratios of $[Ru(dpp)_3]^{2+}$ and $[Ru(bpy)_3]^{2+}$. The excited-state lifetimes of $[Ru(dpp)_3]^{2+}$ and $[Ru(bpy)_3]^{2+}$ differ by 10-fold, allowing us to tune the sensor response ($\tau_0$ tunability per Eqn. 1). [Note: Since we are forming xerogels that are doped with two luminophores that exhibit different $\tau_0$ values, it is not rigorously correct to use the term $\tau_0$. To be rigorous one should use the term $<\tau_0>$ ($=f_{dpp}\tau_{0dpp}+f_{dpy}\tau_{0dpy}$). In this expression, $f_x$ represents the fraction of the total intensity arising from luminophore x (dpp or bpy) and $\tau_{0x}$ is the excited-state luminescent lifetime of luminophore x (dpp or bpy) in the absence of quencher.]

The actual response curves from these five sensors, as a function of gaseous and dissolved $O_2$, are presented in FIGS. 16A and 16B, respectively. The differential response is obvious as is the fact that the xerogels that contain both $[Ru(dpp)^{2+}]+$ and $[Ru(bpy)_3j^{2+}$ (Sensors B-D) exhibit non-linear Stern-Volmer plots.

Figure 17:
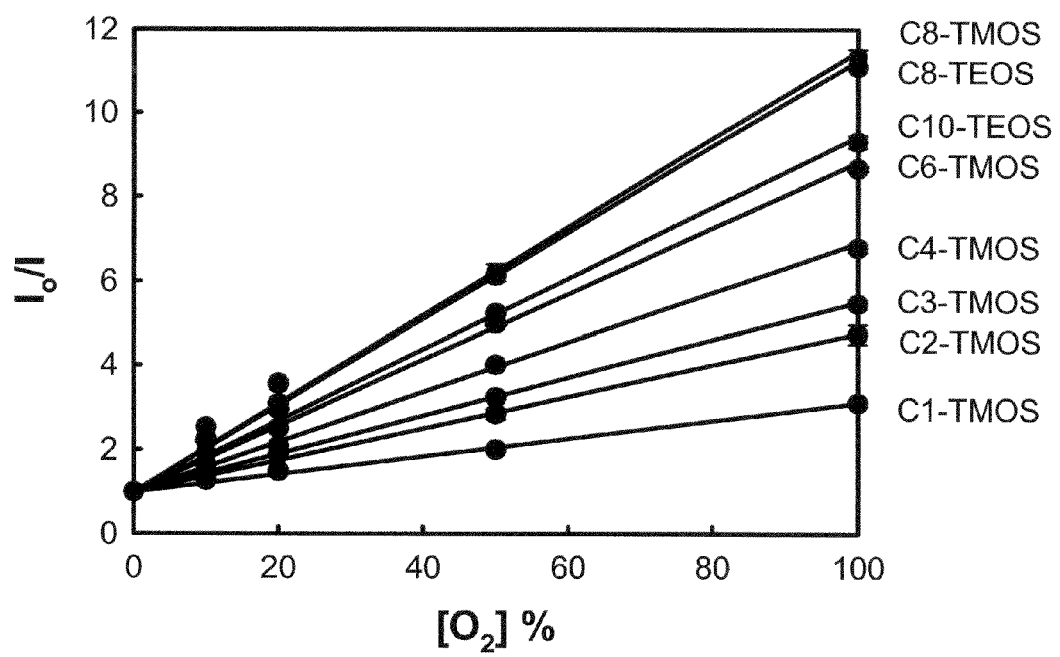
FIG. 17 shows calibration curves for another type of diversified, xerogel-based sensor library. The luminophore is identical in these sensor elements. The individual sensors are derived from equal molar mixtures of $c_n$-TMOS and TMOS or $c_n$-TEOS and TEOS. This is an example of kq-based diversification.

FIG. 17 presents the response profiles from a portion of another diversified $O_2$ responsive sensor library. Here, we show results from eight sensors each designed for $O_2$ as a function of added gaseous $O_2$. These specific sensors were fabricated from a binary xerogel composed of identical molar ratios of TEOS and $C_1$-$C_{12}$-TriEOS or TMOS and $C_1$-$C_{12}$-TriMOS. The luminophore is $[Ru(dpp)_3]^{2+}$. The $[Ru(dpp)_3]^{2+}$ excited-state luminescence lifetime is independent of the xerogel composition; however, the bimolecular quenching constant within these xerogel composites differ by 10-fold. Thus, we can tune the sensor response (kq tunability per Eqn. 1).

Figure 16:
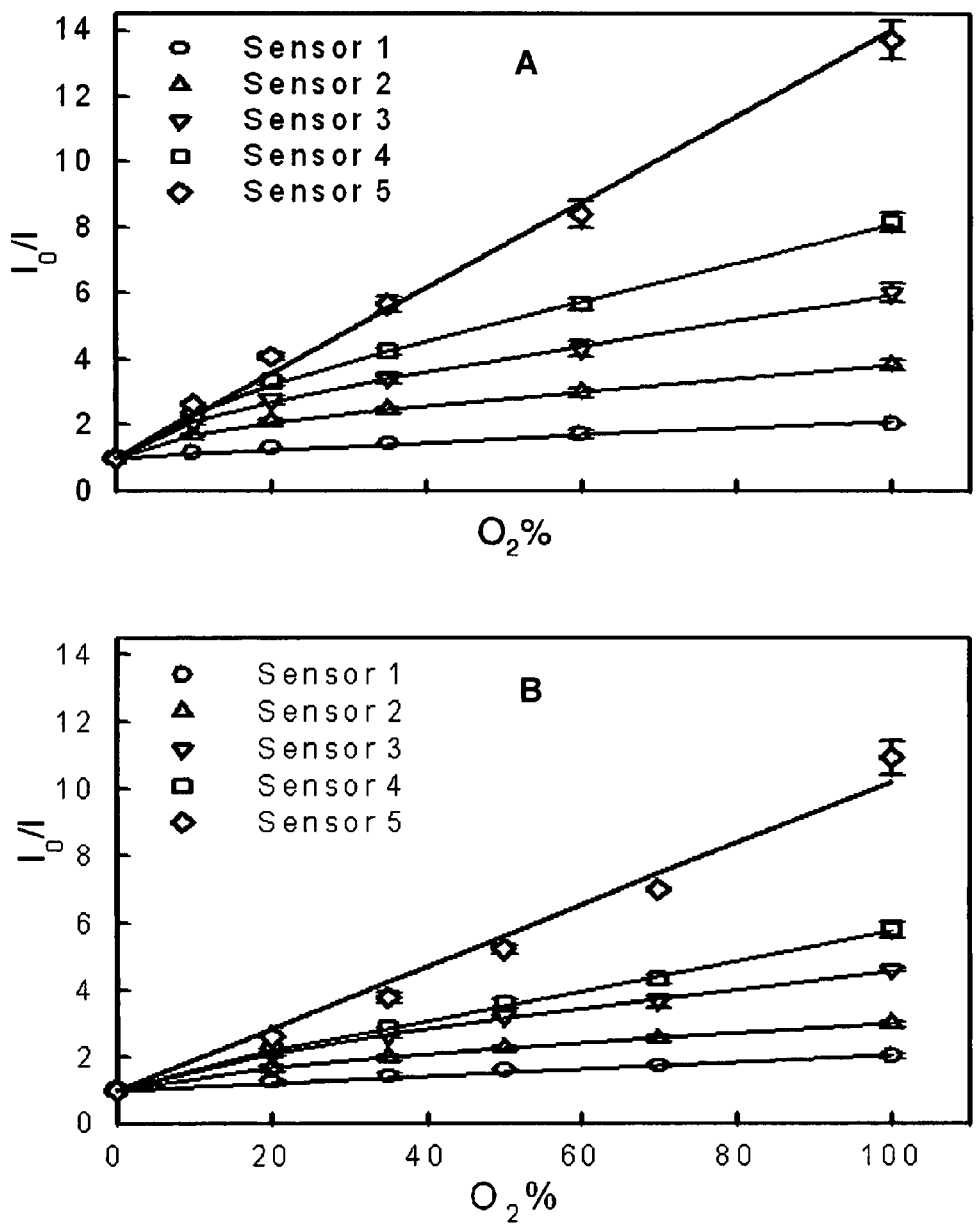
FIG. 16 shows calibration curves for the sensor elements shown in FIG. 1. (panel A) gaseous $O_2$ (panel B) dissolved $O_2$.

FIGS. 15-17 illustrate the diversified xerogel-based analyte sensing strategy. Tables 1 and 2 show the improvement in accuracy realized by using this diversified sensor scheme.

TABLE 1

Comparison of individual and collective sensor accuracy for gaseous $O_2$.

| Sensor | Unknown = 45% $O_2$ | Unknown = 85% $O_2$ |
| --- | --- | --- |
| A | 48.0 ± 3.3 | 80.4 ± 3.3 |
| B | 46.6 ± 5.1 | 86.9 ± 7.7 |
| C | 44.0 ± 22 | 82.6 ± 7.6 |
| D | 44.4 ± 1.7 | 84.6 ± 4.5 |
| E | 45.4 ± 1.9 | 82.3 ± 3.0 |
| All 5 Sensors | 45.4 + 1.9 | ~3.3 ± 2.5 |

TABLE 2

Comparison of individual and collective sensor accuracy for dissolved $O_2$.

| Sensor | Unknown = 40% $O_2$ | Unknown = 80% $O_2$ |
| --- | --- | --- |
| A | 44.1 ± 10.3 | 79.1 ± 11.9 |
| B | 43.6 ± 2.8 | 83.2 ± 2.5 |
| C | 40.2 ± 2.2 | 81.8 ± 7.2 |
| D | 41.5 ± 3.2 | 80.1 ± 5.4 |
| E | 39.1 ± 1.6 | 78.1 ± 2.9 |
| All 5 Sensors | 41.7 ± 2.2 | 80.4 ± 2.0 |

Example 4

Chemical Reagents. Tris(4,7'-diphenyl-1,10'-phenanthroline)-ruthenium(II) chloride pentahydrate was purchased from GFS Chemicals, Inc. and purified as described in the literature. TEOS and Octyl-triEOS were purchased from United Chemical Technologies. HCl was obtained from Fisher Scientific Co. EtOH was a product of Quantum Chemical Corp. All reagents were used as received unless mentioned otherwise. Deionized water was prepared to a specific resistivity of at least 18 MΩcm by using a Barnstead NANOpure II system.

Preparation of $[Ru(dpp)_3]^{2+}$-Doped Octyl-triEOS/TEOS Composite Xerogel Sensing Films. A pure TEOS-derived sol was prepared by mixing TEOS (3.345 mL, 15 mmol), water (0.54 mL, 30 mmol). EtOH (3.4 mL. 60 mmol), and I-lCl (15 aL of 0.1 M HCl, 0.0015 mmol). This sol solution was then capped and magnetically stirred under ambient conditions for 6 h. This particular formulation was chosen because it is representative of TEOS-based xerogels reported in the literature The Octyl-triEOS/TEOS composite sols were prepared by mixing TEOS and Octyl-triEOS (6.5 mmol in total) together to form solutions that contained 20, 40, 50. 60, or 80 mol % Octyl-triEOS. These particular precursors were selected to provide a wide range of physicochemical properties in the final xerogels. To each of these sol solutions we added EtOH (1.25 mL, 22 mmol) and HCl (0.4 mL of 0.1 N HCl, 0.04 mmol). These solutions were then capped and magnetically stirred under ambient conditions for 1 h. These solutions were then diluted 1:1 (v/v) with EtOH. We found that the EtOH dilution step was necessary to lower the overall solution viscosity, slow the onset of gelation, and improve the final spin-coated film quality.

The luminophore-doped sol solutions were prepared by mixing 60 μL of 2 mM $[Ru(dpp)_3]^{2+}$ (in EtOH) with 540 4 of the corresponding sol solution (vide supra). Blanks were prepared by omitting the $[Ru(dpp)_3]^{2+}$ These sol mixtures were capped and magnetically stirred under ambient conditions for 10 mm prior to spin casting.

Xerogel films were formed by spin casting onto 2.5 cm×2.5 cm glass microscope slides. Each slide was first cleaned by soaking in 1 M NaOH for 24 h. All slides were rinsed with copious amounts of deionized water and EtOH and dried under ambient conditions. Films were formed by delivering 100 4 of a given sol solution onto a glass slide placed in the spin coater. The spin coater was then engaged and the rotational velocity adjusted to 3000 rpm. Spinning was continued for 30s. All films were stored in the dark under ambient conditions for the long-term aging studies. The aging time clock begins immediately after a film is cast. Experiments were conducted over an 11-month period.

Profilometry measurements were performed at regular time intervals on films that had aged for between 1 week and 11 months. There was no more than a 10% change in the individual film thickness over 11 months.

Samples and blanks were prepared in triplicate on five separate occasions by using fresh reagent batches. The average and standard deviation for all measurements (n=15) are reported. The blank contribution was <1% of the observed luminescence when the xerogels were subjected to 100% O2.

Instrumentation. A Hitachi model S-4000 field emission scanning electron microscope (SEM) was used to record the film images. The accelerating voltage was maintained at 20 kV.

All steady-state fluorescence measurements were carried out by using an SLM-Aminco model 48000 MHF spectrofluorometer. A xenon arc lamp was used as the excitation source ($\lambda_{ex}$=475 nm). The excitation radiation impinged on the film-coated side of the glass substrates at an incident angle of ~60° with a 90° angle maintained between the excitation beam trajectory and the emission collection optics.

The emission was monitored through a 570-nm long-pass filter as we gradually adjusted the environment surrounding the sample from pure $N_2$ to pure $O_2$—We typically allow 30s between changes in the $N_2/O_2$ concentration to ensure that a new equilibrium point had been established. Equilibrium was evident when the luminescence intensity remained constant to within +2%. There was no hysteresis observed. The $O_2$ concentrations were accurate to ±1%. Response times were <5 s.

The time-resolved intensity decay measurements were performed by using an $N_2$-pumped dye laser as the excitation source (Photon Technology International, model GL-301 dye and model GL-3300 pump). The dye laser output was adjusted to 448 nm. The sample emission was passed through a 570-nm long-pass filter and detected with a photomultiplier tube (Hamamatsu, model R928). The photomultiplier tube output (terminated into 50 Q) was connected to a 200-MI-lz digital oscilloscope (Tektroniz. model TDS 350) that was interfaced to a personal computer. During theses measurements, a pure gas or gas mixture was used to purge the entire sample chamber for 5 mm and 10-20 data sets were collected when the total area under a intensity decay profile remained constant (+2%). A CVI LabWindows software program was used to acquire the data. The intensity decay profiles were analyzed by using SigmaPlot version 3.0 (Jandel Scientific). The short instrument response function (-~-20 ns). combined with the long $[Ru(dpp)_3]^{2+}$ excited-state luminescence lifetime (>3 μs), removes the need for deconvolution.

Figure 18:
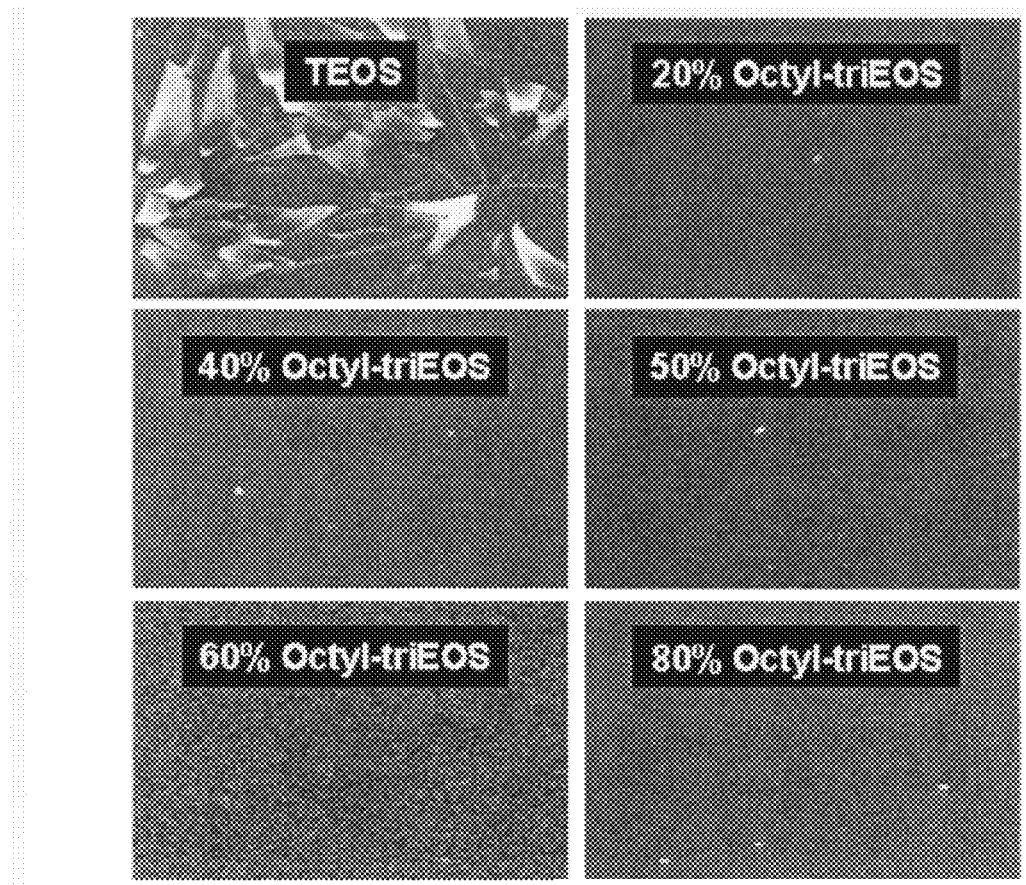
FIG. 18 shows low-resolution SEM images of xerogel films. The TEOS film is 2 months old; all other films are 3 months old. Film age does not affect the SEM images.

SEM Images. The surface structure of a sensor platform is generally important to its sensitivity and reliability. FIG. 18 is a series of SEM micrographs of pure TEOS and Octyl-triEOS/TEOS composite xerogel films. Significant cracking was always observed for the pure TEOS-based xerogel films. In contrast, all the Octyl-triEOS/TEOS composite xerogel films appear, at this magnification, to be smooth and crack free. Profilometry experiments showed that the Octyl-triEOS/TEOS composite xerogel films were 1.0+0.1 μm thick.

Figure 19:
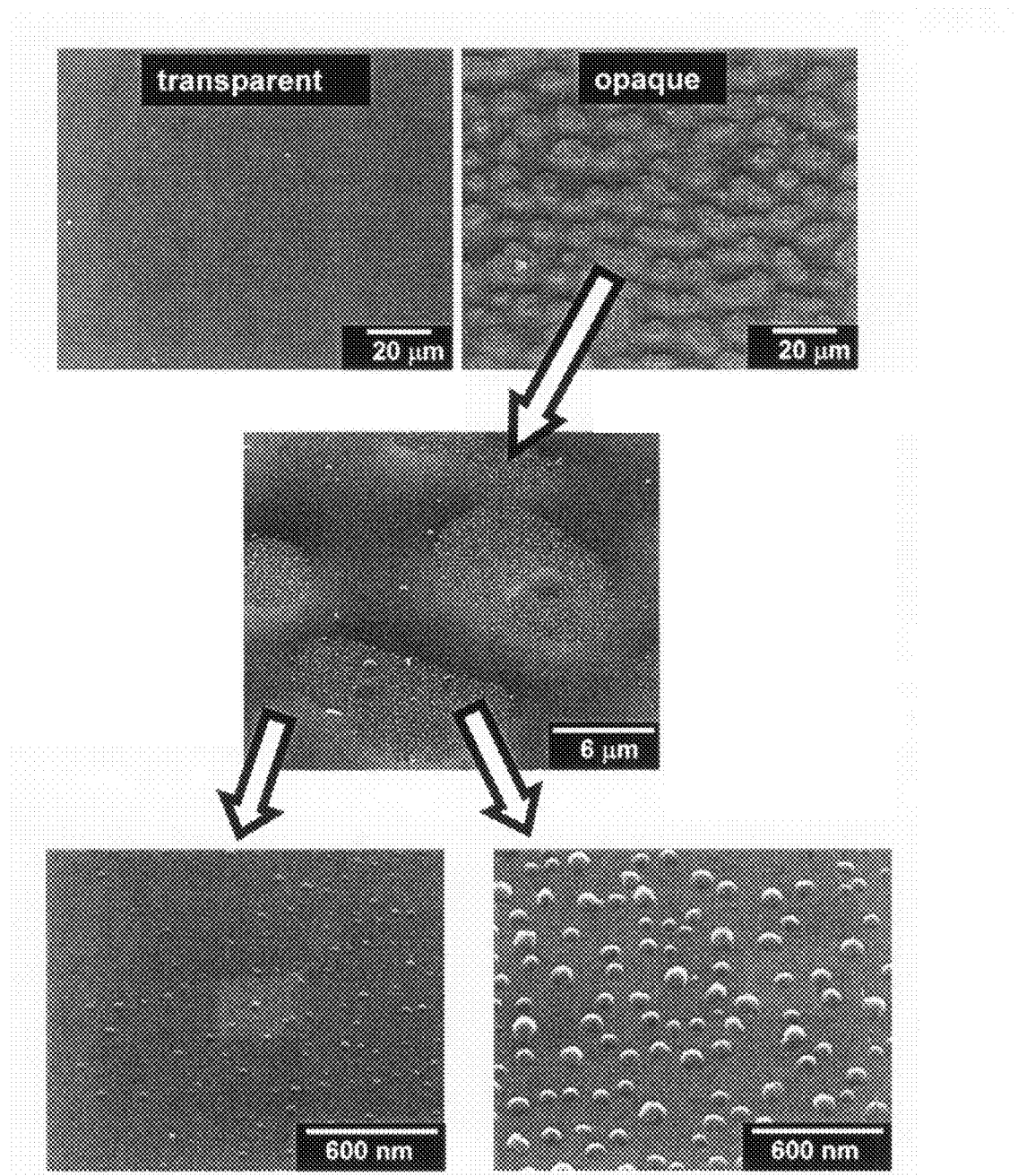
FIG. 19 shows high-resolution SEM images of various regions within a typical 60 mol % octyl-triEOS/40 mol % TEOS composite xerogel film showing domain separation and heterogeneity. These films are 3 months old. Film age does not affect the SEM images.

Higher resolution SEM micrographs (FIG. 19) showed that certain composite xerogel films (e.g., ≧60 mol % Octyl-triEOS) were not particularly uniform. The surface of these composite xerogels were characterized by two regions: (1) homogeneous and transparent and (2) heterogeneous and opaque. The transparent regions were thicker on average and they were characterized by a few small (50-60-nm diameter), uniform raised features on a more or less uniform base. The opaque region was much less thick, and it was characterized by a less uniform set of larger (50-200-nm diameter) features on the glass substrate base.

Figure 20:
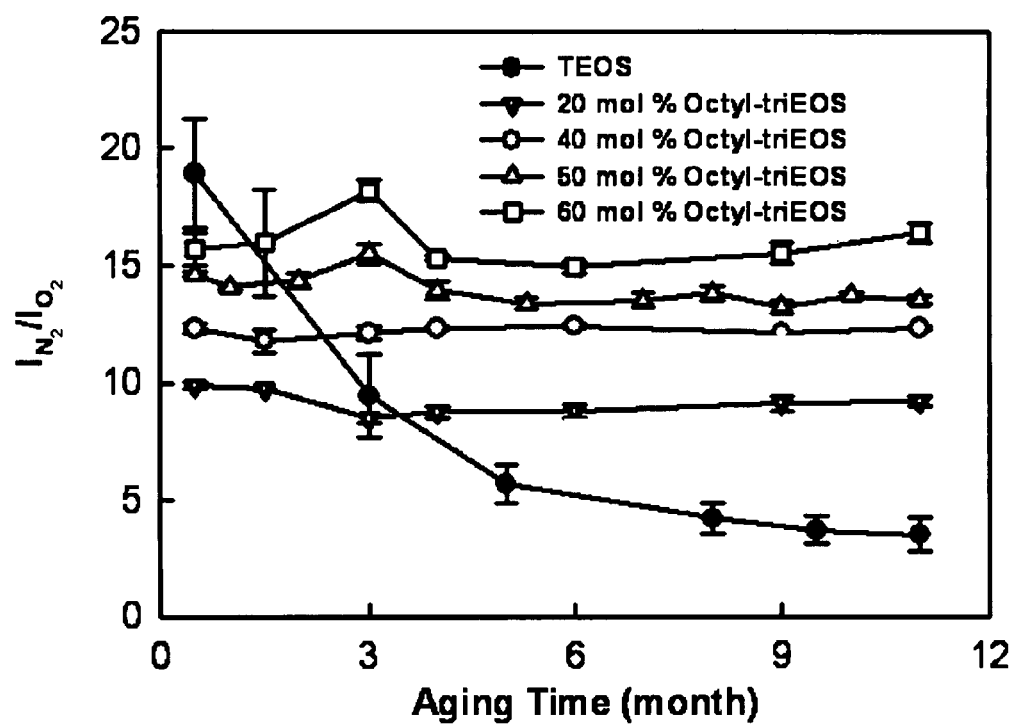
FIG. 20 shows effects of storage/aging time and xerogel composition on the average $O_2$ sensitivity.

Average Sensitivity and Stability. In FIG. 20, we report the effects of aging time and xerogel composition on the O2 sensor's average sensitivity and response stability. At early times following sensor fabrication, the pure TEOS-based xerogels exhibit the greatest $I_{N2}/I_{O2}$ of any sensor tested. However, as this xerogel ages, the sensitivity decreases by almost 5-fold ($I_{N2}/I_{O2}$=19 at 2 weeks and $I_{N2}/I_{O2}$=4 at 11 months). Thus, the pure TEOS-based sensor drifts with time, losing significant sensitivity with time. This type of behavior has also been observed with pyrene-doped TEOS-based xerogels.

The Octyl-triEOS/TEOS composite xerogels exhibit sensitivities that depend on the mole percent Octyl-triEOS in the xerogel. The greatest sensitivity is seen for those xerogels that contain the higher Octyl-triEOS mole percent. We attribute the increasing sensitivity to the nonbridging Si—$C_8H_{17}$ bonds that act as network modifiers, increasing the overall xerogel hydrophobicity and terminating the silicate network.

The sensitivity of the Octyl-triEOS/TEOS composite xerogels are remarkably stable over the course of 11 months. For example, over the course of an 11-month stability study, the 20, 40. and 60 mol % Octyl-triEOS composites, exhibit $I_{N2}/I_{O2}$ values of 8.99+0.49 (RSD 5.5%), 12.06+0.19 (RSD=1.5%), and 16.48+1.14 (6.9% RSD), respectively. For the 50 mol % Octyl-triEOS composites, over the same time period. the $I_{N2}/I_{O2}$ was 14.37+0.58 (RSD=4.0%). Together these results show that sensors based on the Octyl-triEOS/TEOS composite xerogels exhibit excellent long-term stability and sustained high sensitivity in comparison to a pure TEOS-based xerogel sensor. The Octyl-triEOS/TEOS xerogel films are reportedly more flexible in comparison to the pure TEOS-base films. Given this, we speculate that the observed improvements in sensor long-term stability and sustained high sensitivity arise from the increased flexibility that overcomes the xerogel shrinkage and pore collapse with time.

Figure 21:
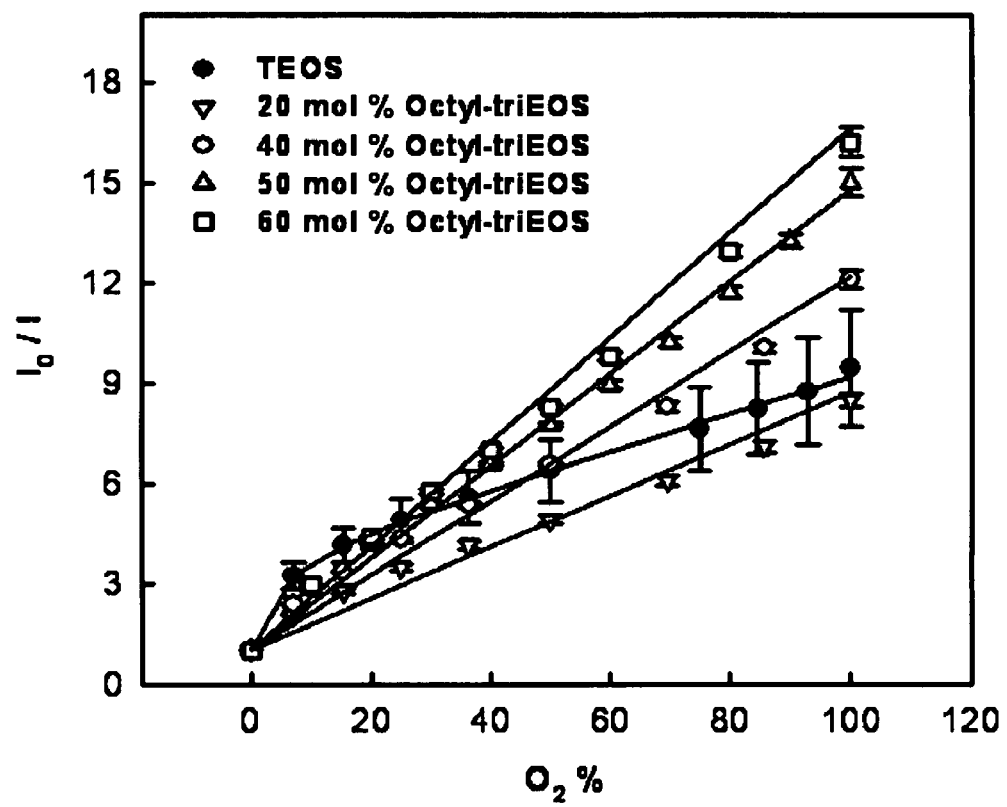
FIG. 21 shows typical intensity-based Stern-Volmer plots for 3-month old $[ru(dpp)_3]^{2+}$-doped octyl-triEOS/TEOS composite xerogels. The solid lines represent the best fit to a Demas (TEOS) or Stern-Volmer model (all others).

Stern-Volmer Plots. FIG. 21 presents typical intensity-based Stern-Volmer plots for a randomly selected set of 3-month-old $[Ru(dpp)_3]^{2+}$-doped xerogel films. The solid lines represent the best fits to the data. The recovered fitting parameters are compiled in Table 3.

TABLE 3

Effect of Compositions and Aging Time on the $O_2$ Quenching of $[Ru(dpp)_3]^{2+}$ - doped Octyl-triEOS/TEOS Xerogels[a]

| Octyl-triEOS (mol %) | aging time[b] | Stern-Volmer | | Lehrer | | | | Demas[c] | | |
|---|---|---|---|---|---|---|---|---|---|---|
| | | $K_{SV}([O_2]^{-1})$ | $r^2$ | $f_q^d$ | $K_{SVq}^2([O_2]^{-1})$ | $r^2$ | $f_1$ | $K_{SV1}([O_2]^{-1})$ | $K_{SV2}([O_2]^{-1})$ | $r^2$ |
| 0 | 3 m | 0.094 ± 0.008 | 0.9030 | 0.92 ± 0.01 | 0.284 ± 0.040 | 0.9784 | 0.76 ± 0.02 | 1.02 ± 0.001 | 0.013 ± 0.001 | 0.9982 |
| | 5 m | 0.050 ± 0.003 | 0.9430 | 0.88 ± 0.01 | 0.116 ± 0.015 | 0.9792 | 0.55 ± 0.02 | 0.68 ± 0.18 | 0.016 ± 0.001 | 0.9988 |
| 20 | 6 w | 0.086 ± 0.003 | 0.9872 | 0.97 ± 0.04 | 0.107 ± 0.025 | 0.9866 | 0.36 ± 0.20 | 5.0 ± 48 | 0.050 ± 0.014 | 0.9021 |
| | 11 m | 0.077 ± 0.004 | 0.9876 | 0.96 ± 0.03 | 0.115 ± 0.017 | 0.9873 | 0.52 ± 0.23 | 0.69 ± 0.06 | 0.032 ± 0.007 | 0.9895 |

TABLE 3-continued

Effect of Compositions and Aging Time on the $O_2$ Quenching of [Ru(dpp)$_3$]$^{2+}$ - doped Octyl-triEOS/TEOS Xerogels[a]

| Octyl-triEOS (mol %) | aging time[b] | Stern-Volmer $K_{SV}([O_2]^{-1})$ | $r^2$ | $f_q$[d] | Lehrer $K_{SVq}^2([O_2]^{-1})$ | $r^2$ | $f_1$ | Demas[c] $K_{SV1}([O_2]^{-1})$ | $K_{SV2}([O_2]^{-1})$ | $r^2$ |
|---|---|---|---|---|---|---|---|---|---|---|
| 40 | 6 w | 0.110 ± 0.003 | 0.9896 | | | | | | | |
|    | 11 m | 0.112 ± 0.004 | 0.9877 | | | | | | | |
| 50 | 3 m | 0.138 ± 0.002 | 0.9932 | | | | | | | |
|    | 11 m | 0.126 ± 0.003 | 0.9904 | | | | | | | |
| 60 | 6 w | 0.142 ± 0.004 | 0.9905 | | | | | | | |
|    | 11 m | 0.156 ± 0.004 | 0.9826 | | | | | | | |

[a]When an entry is not given, the Stern-Volmer model is the best model.
[b]m, months: w, weeks.
[c]Terms are from eq 2.
[d]$f_q$, fraction of luminophore that is quenchable.
[e]$K_{SVq}$, Stern-Volmer quenching constant of luminophore that is quenchable.

Inspection of these results reveal several key points. First, the Stern-Volmer plot for the pure TEOS-based xerogel exhibits downward curvature and the fit to the Stern-Volmer model (eq 1) is poor ($r^2$=0.9030). Superior fits are achieved for the Leherer and Demas models, the Demas model offering the best fit of the three models tested ($r^2$=0.9982). These results are fully in line with the behavior of a wide variety of luminophore. doped sol-gel derived xerogels. Second. the Stern-Volmer plots for the Octyl triEOS/TEOS composite xerogel films are reasonably well described by eq 1. That is, is it not necessary to use the more complex Lehrer or Demas models to describe the Stern-Volmer plots for the Octyl-triEOS/TEOS composite xerogels. (Note: These particular 20 mol % Octyl-triEOS data appear to deviate from the Stern-Volmer model at low $O_2$ concentrations; however. $r^2$ does not improve significantly for the Lehrer or Demas models and the imprecision in the recovered parameters is always large for these more complex models for this xerogel.) Together these results demonstrate that the microenvironment that surrounds the [Ru(dpp)$_3$]$^{2+}$ molecules changes from being heterogeneous within the pure TEOS-based xerogel to being more homogeneous within composite xerogels that contain >20% Octyl-triEOS. The linearity of the Stern-Volmer plots open a door to simple two point calibration strategies. Third, the recovered $K_{8\sim}$ values (Table 3) for the pure TEOS-based xerogel films decrease as the film age increases. The recovered Ksv values for the Octyl-triEOS/TEOS composite xerogel films do not suffer this problem; they exhibit excellent long term stability. This result is entirely consistent with FIG. 20. Finally, inspection of FIG. 21 shows that the error bars associated with the pure TEOS-based xerogel films are 3-10-fold larger in comparison to the Octyl-triEOS/TEOS composite xerogel films. This result demonstrates that the film-to-film reproducibility is significantly better for the composite xerogels in comparison to the pure TEOS-based xerogels.

Figure 22:
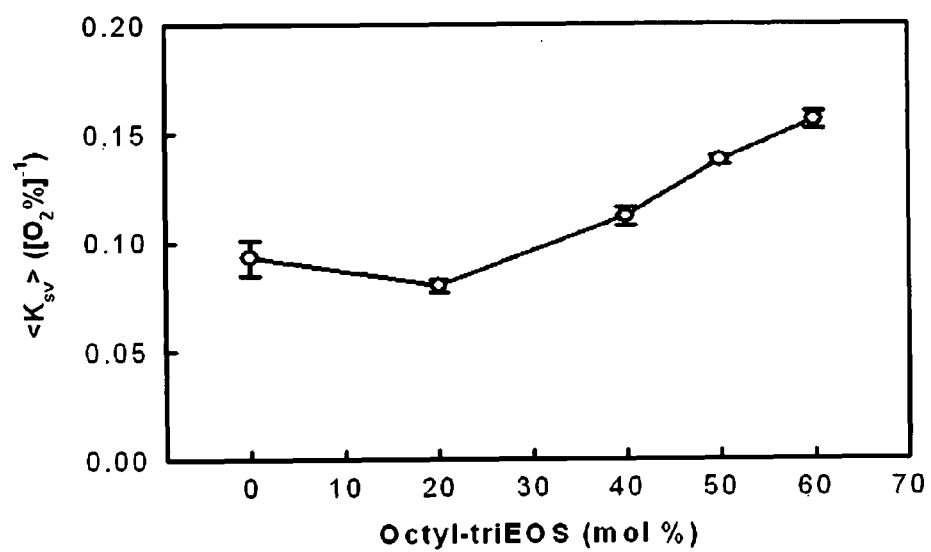
FIG. 22 shows effects of xerogel composition on the average Stern-Volmer quenching constant. The films are 3 months old.

In FIG. 22, we report the effects of xerogel composition on the average Stern-Volmer quenching constant, <Ksv>. These results show that <$K_{sv}$> increases as we increase the mole percent Octyl-triEOS in the xerogel. To explore the origin of the improved sensitivity, we carried out a series of time resolved intensity decay experiments.

Figure 23:
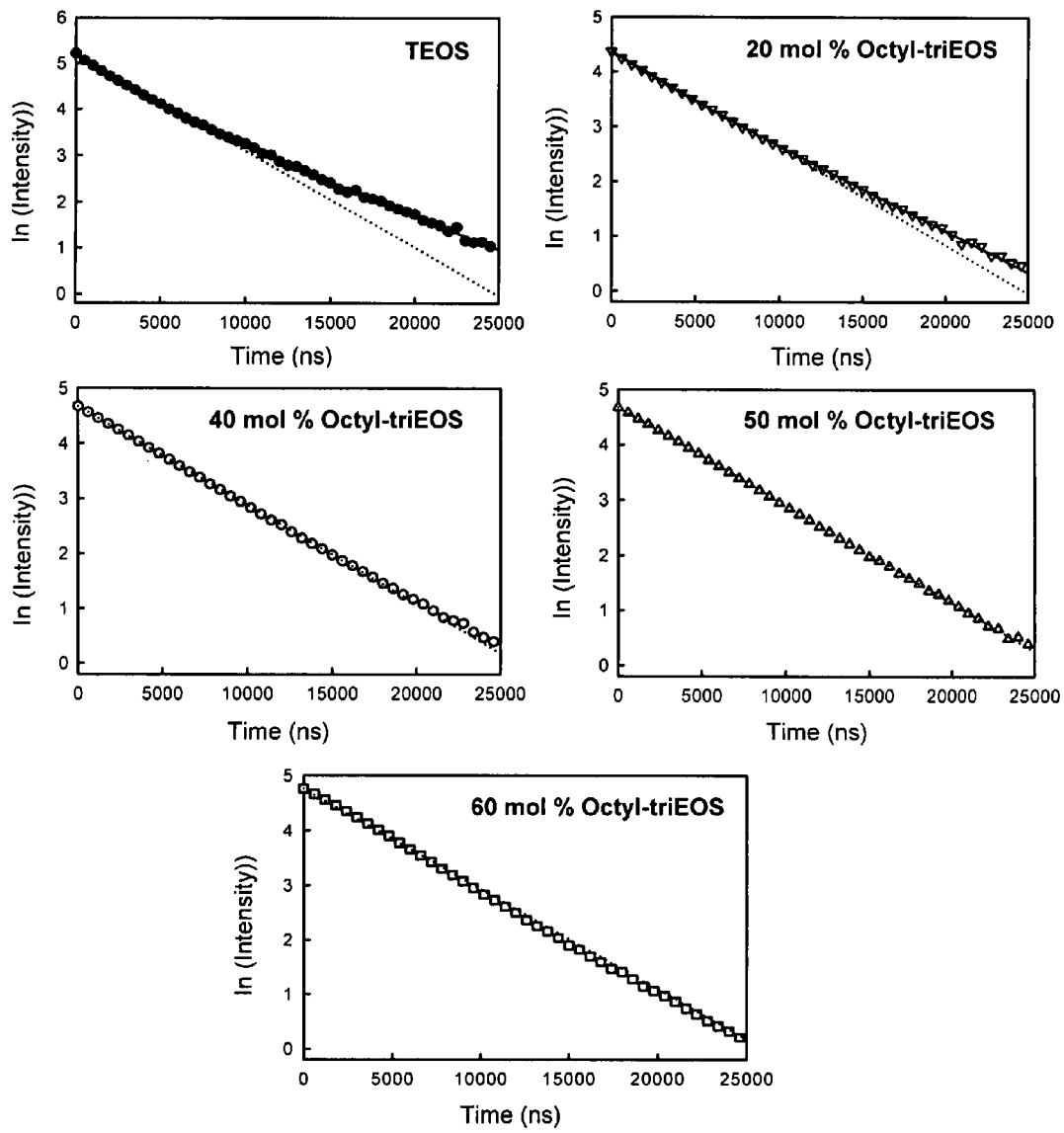
FIG. 23 shows typical time-resolved intensity decay traces and fits (lines) for 3-month $[Ru(dpp)_3]^{2+}$-doped octyl-triEOS/TEOS composite xerogels in a pure $N_2$ environment. The $[Ru(dpp)_3]^{2+}$-doped intensity decay is clearly biexponential for the pure TEOS and 20 mol % octyl-triEOS composite xerogels. The $[Ru(dpp)_3]^{2+}$ intensity decay is single exponential in those xerogels that contain >20 mol % octyl-triEOS.

Time-Resolved Intensity Decays. FIG. 23 presents a representative series of time-resolved intensity decay traces for 3-month-old [Ru(dpp)$_3$]$^{2+}$±doped xerogels when they are maintained in a pure $N_2$ atmosphere along with fits to single- and double-exponential decay models. The recovered decay terms are collected in Table 4.

TABLE 4

Effects of Octyl-triEOS/TEOS Xerogel Composition on the Recovered [Ru(dpp)$_3$]$^{2+}$ Time-Resolved Intensity Decay Kinetics.

| Octyl-triEOS (mol %) | $f_1$[b] | $r_1$ (ns) | $r_2$ (ns) | $r^2$ |
|---|---|---|---|---|
| 0 | 1.00 | 4773 ± 18 | | 0.6585 |
|   | 0.46 ± 0.01 | 2741 ± 48 | 6872 ± 77 | 0.9967 |
| 20 | 1.00 | 5660 ± 11 | | 0.9872 |
|    | 0.25 ± 0.01 | 2983 ± 59 | 6668 ± 32 | 0.9929 |
| 40 | 1.00 | 5569 ± 2 | | 0.9993 |
| 50 | 1.00 | 5645 ± 4 | | 0.9982 |
| 60 | 1.00 | 5453 ± 8 | | 0.9978 |

[a]Samples were aged for 3 months.
[b]$f_1 + f_2 = 1$.

These results clearly demonstrate that the [Ru(dpp)$_3$]$^{2+}$ time-resolved intensity decay is multiexponential in the pure TEOS-based xerogel. This is common for luminophores doped in a wide variety of host matrices. As the mole percent of Octyl triEOS in the composite xerogel increases, the time-resolved intensity decay traces become single exponential. To the best of our knowledge, these represent the first luminophore-doped xerogels with >20 mol % OctyltriEOS that exhibit purely single-exponential intensity decay traces and linear Stern-Volmer plots (FIG. 21). Taken together, these results argue that the microenvironment surrounding the [Ru(dpp)$_3$]$^{2+}$ molecules is homogeneous within those Octyl-triEOS/TEOS xerogel composites that contain more than 20 mol % Octyl-triEOS. The fact that the Stern-Volmer plots appear to be "linear" for the 20 mol % Octyl-triEOS xerogels (Table 3) while the intensity decay traces are clearly multi-exponential is a manifestation of the increased information content of the time-resolved measurements in comparison to a simple intensity measurement.

Figure 24:
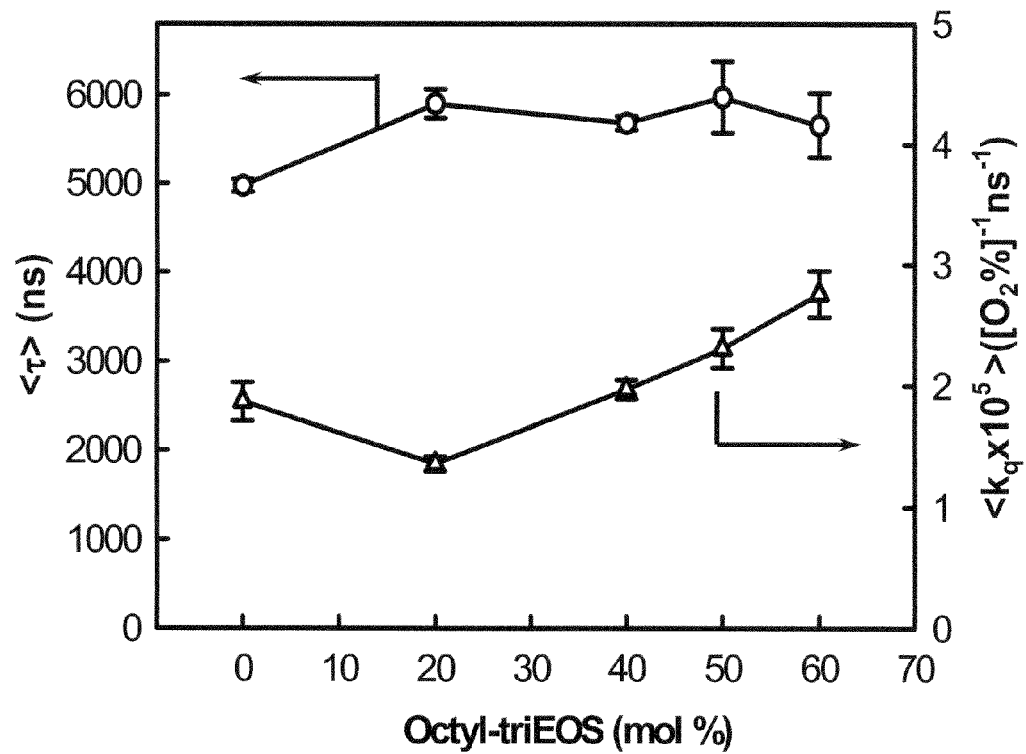
FIG. 24 shows effects of xerogel composition on the average $[Ru(dpp)_3]^{2+}$ excited-state fluorescence lifetime $<<\tau>=\Sigma$ ($f_i\tau_i$) and the bimolecular quenching constant. The films are 3 months old.

The sensitivity of any quenchometric $O_2$ sensor depends on the Stern-Volmer quenching constant, Ksv, which in turn depends on two factors (eq 1): $v_0$ and A~. FIG. 24 summarizes the effects of Octyl-triEOS mole percent on the average $\tau_0$ and $k_q$ (i.e., <$\tau_0$> and <$k_q$>) values for 3-month-old xerogels. These results show that <to > increases from ~'5µs in the pure TEDS-based xerogel film to "~6 us for 60 mol % Octyl-triEOS/TEOS composite, a 20% increase. Thus, the increase in the [Ru(dpp)$_3$]$^{2+}$ luminescence lifetime alone is not entirely responsible for the 50% increase in $O_2$ sensitivity for the Octyl-triEOS/TEOS composites. The remaining cause of the increased sensitivity (30%) arises from an increase in <kq>. Thus, 40% of the total improvement in $O_2$ sensitivity arises from an increase in $[Ru(dpp)_3]^{2+}$'s excited-state lifetime within the Octyl-triEOS/TEOS xerogel composites and 60% comes about from a concomitant increase in <$k_{,1}$> (i.e., $O_2$ transport within the Octyl-triEOS/TEOS xerogel composites).

Example 4 illuminates the quenchometric behavior of $[Ru(dpp)_3]^{2+}$ sequestered within a series of Octyl-triEOS/TEOS composite xerogel films. Upon adding Octyl-triEOS to TEDS, a number of changes occur. First, the quality of the films improve from being cracked (pure TEDS) to being uniform and crack free (composites that contain 20-50 mol % Octyl-triEQS). Second, the $O_2$ sensor long-term stability is improved significantly by adding the OctyltriEOS component. Over a period of 11 months, the sensitivity for a pure TEDS-based sensor drops by 400% whereas a 50 mol % Octyl-triEOS/TEOS composite xerogel remains unchanged (RSD=4%). Third, the average $O_2$ sensitivity ($I_{N2}/I_{O2}$) increases as we increase the mole percent Octyl-triTEOS within the composite. In comparison to an 11-month-old TEDS xerogel, a 50 mol % OctyltriEOS/TEOS composite xerogel exhibits a greater than 4-fold improvement in sensitivity. For 3-month-old films, 40% of the observed increase in the observed $O_2$ sensitivity comes about from an increase in the $[Ru(dpp)_3]^{2+}$'s excited-state lifetime and 60% arises from a concomitant increase in $O_2$ transport within the Octyl-triEOS/TEOS xerogel composites (i.e., <kq>). Fourth, based on the Stern-Volmer plots and the time-resolved intensity decay traces, the $[Ru(dpp)_3]^{2+}$ microenvironment surrounding the $[Ru(dpp)_3]^{2+}$ molecules is homogeneous within those Octyl-triEOS/TEOS xerogel composites that contain more than 20 mol % Octyl-triEOS.

We claim:

1. A photonic sensor system for sensing an analyte in a sample, said system comprising:
   a) at least one encapsulated beta emission source;
   b) a scintillation layer which radiates upon exposure to beta emission from said beta emission source;
   c) an array of sensors formed on or within the scintillation layer and which comprise luminophores capable of radiating upon exposure to radiation from said scintillation layer, wherein the intensity, wavelength, polarization, spectrum, or lifetime of said luminophore radiation is changed upon exposure of the sensors to said analyte, wherein at least two sensors in the array have different calibration curves with respect to said analyte, wherein each of said different calibration curve provides a single analyte concentration value for a given change in luminophore radiation, and the individual signals from each of the at least two distinct sensors are detected simultaneously;
   wherein the scintillating layer is disposed between the beta emission source and said array of sensors; and
   wherein said array of sensors is positioned with respect to the scintillation layer such that the scintillation layer radiation impinges each sensor of the array without having first impinged other sensors in the array.

2. A photonic sensor system as in claim 1 wherein the beta emission source is encapsulated within a ceramic or steel matrix.

3. A photonic sensor system as in claim 1 wherein the beta emission source is $^{90}$Sr.

4. A photonic sensor system as in claim 1 wherein the sensors in the array comprise a xerogel.

5. A photonic sensor system as in claim 4 wherein the xerogels in at least two of the sensors in the array are different from each other.

6. A photonic sensor system as in claim 1 wherein said luminophores in at least two of the sensors in the array are different from each other.

7. A photonic sensor system as in claim 4 wherein the analyte is oxygen, and wherein said array of sensors comprise tris(4,7-diphenyl-1,10-phenanthroline)ruthenium(II), n-octyltriethoxysilane, and tetraethoxysilane.

8. The system of claim 1, wherein the calibration curves are linear.

9. A photonic sensor system for sensing an analyte in a sample, said system comprising:
   a) at least one encapsulated beta emission source;
   b) a scintillation layer which radiates upon exposure to beta emission from said beta emission source;
   c) an array of sensors formed on or within the scintillation layer, said sensors comprising luminophores sequestered in xerogel, said luminophores being capable of radiating upon exposure to radiation from said scintillation layer, wherein the intensity, wavelength, polarization, spectrum, or lifetime of said luminophore radiation is changed upon exposure of the sensors to said analyte, wherein at least two sensors in the array have different calibration curves with respect to said analyte, wherein the different calibration curves are generated from sensors formed from different combinations of precursors of the xerogel or different molar ratios of the luminophores, and the individual signals from each of the at least two distinct sensors are detected simultaneously;
   wherein the scintillating layer is disposed between the beta emission source and said array of sensors; and
   wherein said array of sensors is positioned with respect to the scintillation layer such that the scintillation layer radiation impinges each sensor of the array without having first impinged other sensors in the array.

10. The sensor of claim 9, wherein precursors of the xerogel are selected from the group consisting of i) n-alkyl ($C_1$-$C_{12}$)-triethoxysilane and tetraethoxysilane, and ii) n-alkyl ($C_1$-$C_{12}$)-trimethoxysilane and tetramethoxysilane.

11. The sensor of claim 9, wherein the sensors comprise different molar ratios of luminophores selected from the group consisting of $[Ru(dpp)_3]^{2+}$, $[Ru(bpy)_3]^{2+}$ and combinations thereof.

* * * * *

UNITED STATES PATENT AND TRADEMARK OFFICE
CERTIFICATE OF CORRECTION

| | |
|---|---|
| PATENT NO. | : 7,750,294 B2 |
| APPLICATION NO. | : 11/076729 |
| DATED | : July 6, 2010 |
| INVENTOR(S) | : Bright et al. |

Page 1 of 1

It is certified that error appears in the above-identified patent and that said Letters Patent is hereby corrected as shown below:

Column 23, Claim 1, line 52 "scintillating" should read --scintillation--; and

Column 24, Claim 9, line 41 "scintillating" should read --scintillation--.

Signed and Sealed this

Seventh Day of September, 2010

David J. Kappos
*Director of the United States Patent and Trademark Office*